United States Patent [19]
Sawan et al.

[11] Patent Number: 5,869,073
[45] Date of Patent: Feb. 9, 1999

[54] ANTIMICROBIAL LIQUID COMPOSITIONS AND METHODS FOR USING THEM

[75] Inventors: Samuel P. Sawan, Tyngsboro, Mass.; Tadmor Shalon, Brentwood, Mich.; Sundar Subramanyam, Stoneham; Alexander Yurkovetskiy, Acton, both of Mass.

[73] Assignees: Biopolymerix, Inc, Farnham, United Kingdom; Surfacine Development Company, Inc., Tyngsboro, Mass.

[21] Appl. No.: 663,269

[22] PCT Filed: Dec. 19, 1994

[86] PCT No.: PCT/US94/14636

§ 371 Date: Dec. 13, 1996

§ 102(e) Date: Dec. 13, 1996

[87] PCT Pub. No.: WO95/17152

PCT Pub. Date: Jul. 29, 1995

Related U.S. Application Data

[63] Continuation-in-part of Ser. No. 220,821, Mar. 31, 1994, abandoned, which is a continuation-in-part of Ser. No. 170,510, Dec. 20, 1993, Pat. No. 5,490,938.

[51] Int. Cl.⁶ .................................................. A01N 25/32
[52] U.S. Cl. .................. 424/406; 424/404; 424/407; 424/78.34; 424/78.35; 424/617; 424/618; 514/634; 514/635; 523/122
[58] Field of Search .................... 424/404–406, 424/411–415, 422, 446–449, 486, 78.09, 78.12, 78.27, 78.34, 78.35, 617, 618, 630, 639, 641, 644, 646, 649–655, 409, 417; 514/492–505, 634, 635; 523/122; 623/1–4, 7, 9–11

[56] References Cited

U.S. PATENT DOCUMENTS

| | | | |
|---|---|---|---|
| 3,803,810 | 4/1974 | Rosenberg | 55/159 |
| 4,150,171 | 4/1979 | Feldstein | 427/54 |
| 4,304,894 | 12/1981 | Andrews et al. | 526/310 |
| 4,463,880 | 8/1984 | Kramer et al. | 222/189 |
| 4,494,663 | 1/1985 | Bertaud et al. | 215/232 |
| 4,533,068 | 8/1985 | Meierhoefer | 222/189 |

(List continued on next page.)

FOREIGN PATENT DOCUMENTS

| | | | |
|---|---|---|---|
| 1087977 | 10/1980 | Canada | C14C 5/00 |
| 0459498A1 | 12/1991 | European Pat. Off. | A61F 9/00 |
| 2830977A1 | 1/1980 | Germany | A61J 1/100 |
| 3228850A1 | 2/1984 | Germany | B01D 13/04 |
| 3628197A1 | 2/1988 | Germany | A61J 1/00 |
| 61-8104 | 1/1986 | Japan | B01D 13/00 |
| 2-68105 | 3/1990 | Japan | B01D 38/14 |
| 63-218558 | 3/1990 | Japan | B01D 38/14 |

(List continued on next page.)

OTHER PUBLICATIONS

Amos et al., "Surface Modification of Polymers by Photo-chemical Immobilization" (Abstract) The 17th Annual Meeting of the Society for Biomaterials, Scottsdale, AZ, May 1–5, 1991.

Bain et al., "Formation of Monolayer Films by the Spontaneous Assembly of Organic Thiols from Solution onto Gold" *J. Am. Chem. Soc.* 11:321–335 (1989).

Boaroni et al., "Case Study: Development of A Device with An Antimicrobial Treatment", Medical Plastics Today and Tomorrow Proc. Med. Plast. Conf., Publ. Soc. Plastics Engineers, Brookfield, CT, 1990.

(List continued on next page.)

*Primary Examiner*—Neil S. Levy
*Attorney, Agent, or Firm*—Testa, Hurwitz & Thibeault, LLP

[57] ABSTRACT

A liquid composition for applying a non-leachable antimicrobial coating on a surface. The liquid composition consists of a solution, dispersion or suspension of a biguanide polymer reacted with a cross-linking agent to form an adduct, and an antimicrobial metal material. The resulting antimicrobial coating does not release biocidal levels of leachables into surrounding solution.

9 Claims, 3 Drawing Sheets

U.S. PATENT DOCUMENTS

| | | |
|---|---|---|
| 4,563,485 | 1/1986 | Fox, Jr. et al. .......................... 523/113 |
| 4,581,028 | 4/1986 | Fox, Jr. et al. .......................... 623/2 |
| 4,592,920 | 6/1986 | Murtfeldt et al. .......................... 427/2 |
| 4,603,152 | 7/1986 | Laurin et al. .......................... 604/265 |
| 4,612,337 | 9/1986 | Fox, Jr. et al. .......................... 523/113 |
| 4,675,347 | 6/1987 | Mochizuki et al. ...................... 523/122 |
| 4,677,143 | 6/1987 | Laurin et al. .......................... 523/122 |
| 4,769,013 | 9/1988 | Lorenz et al. .......................... 604/265 |
| 4,853,978 | 8/1989 | Stockum .................................... 2/167 |
| 4,882,232 | 11/1989 | Bugnet et al. .......................... 428/613 |
| 4,917,271 | 4/1990 | Kanner et al. .......................... 222/189 |
| 4,933,178 | 6/1990 | Capelli ...................................... 424/78 |
| 4,938,389 | 7/1990 | Rossi et al. .............................. 222/189 |
| 4,973,493 | 11/1990 | Guire ......................................... 427/2 |
| 4,979,959 | 12/1990 | Guire ......................................... 623/66 |
| 5,002,582 | 3/1991 | Guire et al. ............................... 623/66 |
| 5,013,459 | 5/1991 | Gettings et al. ......................... 210/764 |
| 5,019,096 | 5/1991 | Fox, Jr. et al. ............................ 623/1 |
| 5,025,957 | 6/1991 | Ranalletta et al. ...................... 222/189 |
| 5,040,706 | 8/1991 | Davis et al. .............................. 222/541 |
| 5,049,139 | 9/1991 | Gilchrist ................................... 604/265 |
| 5,060,823 | 10/1991 | Perlman .................................... 222/1 |
| 5,069,907 | 12/1991 | Mixon et al. ............................. 424/445 |
| 5,074,440 | 12/1991 | Clements et al. ........................ 222/189 |
| 5,105,993 | 4/1992 | La Haye et al. ......................... 222/189 |
| 5,110,470 | 5/1992 | Yokosawa et al. .................. 210/500.23 |
| 5,232,687 | 8/1993 | Geimer ..................................... 424/45 |
| 5,265,770 | 11/1993 | Matkovich et al. .................... 210/189 |

FOREIGN PATENT DOCUMENTS

| | | | |
|---|---|---|---|
| 2-192937 | 7/1990 | Japan ............................. | B32B 15/08 |
| 3065223 | 3/1991 | Japan ............................. | B01D 69/00 |
| 4-197362 | 7/1992 | Japan ............................. | A61M 25/00 |
| 4-197363 | 7/1992 | Japan ............................. | A61M 25/00 |
| 4-70935 | 11/1992 | Japan ............................. | G06F 11/32 |
| 2254340 | 7/1992 | United Kingdom ............ | C23C 18/20 |
| 2254340A | 10/1992 | United Kingdom ............ | C23C 18/20 |
| 90/05110 | 5/1990 | WIPO ............................. | B67D 5/58 |
| 93/22320 | 11/1993 | WIPO ............................. | C07F 9/09 |

OTHER PUBLICATIONS

Chu et al., "Newly Made Antibacterial Braided Nylon Sutures. I. In Vitro Qualitative and In Vivo Preliminary Biocompatibility Study", *J. Biomed. Materials Res.* 21:1281–1300 (1987).

Clark et al., "Antibacterial Vascular Grafts with Improved Thromboresistance", *Arch. Surg.* 109:159–162 (1974).

Clapper et al., "Covalent Immobilization of Cell Adhesion Proteins and Peptides to Promote Cell Attachment and Growth on Biomaterials" (Abstract), The 16th Meeting of the Society for Biomaterials, Charleston, SC, May 20–23, 1990.

Clapper et al., "Covalent Immobilization of Extracellular Matrix Peptides to Promote Cell Attachment and Growth on Biomaterials" (Abstract), The 16th Meeting of the Society for Biomaterials, Charleston, SC, May 20–23, 1990.

Clapper et al., "Hirudin Immobilization to Produce Antithrombotic Surfaces" (Abstract), Cardiovascular Science and Technology: Basic and Applied, Louisville, KY, Dec. 1–3, 1990.

Colby et al., "Light Activated Polymers for Flexible Surface Modification" (Abstract), Proceedings of the Medical Design and Manufacturing Conference, New York, NY, Jun. 3, 1992.

Davis et al., "Electrode and Bacterial Survival with Iontophoresis in Synthetic Urine" *J. Urology* 147:1310–1313 (1992).

Dunkirk et al., "Photochemical Coatings for the Prevention of Bacterial Colonization" *J. Biomaterials Applications* 6:131–156 (1991).

Dunkirk et al., "Contact Lens Coatings for Increased Wettability and Reduced Deposits and Bacterial Colonization" (Abstract), The 16th Annual Meeting of the Society for Biomaterials, Charleston, SC, May 20–23, 1990.

Erck et al., "Adhesion of Silver Films to Ion–Bombarded Zirconia" *Lubrication Engineering* 47(8):640–644 (1991).

Erdemir et al., "Ion–Assisted Deposition of Silver Films on Ceramics for Friction and Wear Control" *J. Soc. Tribologists and Lubrication Engineers* pp. 23–30 (1990).

Farrah et al., "The Production of Antibacterial Tubing, Sutures and Bandages by in Situ Precipitation of Metallic Salts" *Can. J. Microbiol.* 37:445–449 (1991).

Gravens et al., "The Antibacterial Effect of Treating Sutures with Silver" *Surgery* 73(1):122–127 (1973).

Herruzo–Cabrera, R., "Evaluation of the Penetration Strength, Bactericidal Efficacy and Spectrum of Action of Several Antimicrobial Creams Against Isolated Microorganisms in A Burn Centre", *Burns* 18(1):39–44 (1992).

Laibinis et al., "Comparison of the Structures and Wetting Properties of Self–Assembled Monolayers of n–Alkanethiols on the Coinage Metal Surfaces, Cu, Ag, $Au^{1}$", *J. Am. Chem. Soc.* 113:7152–7167 (1991).

Leung et al., "Decreased Bacterial Adherence to Silver–Coated Stent Material: An in Vitro Study" *Gastrointestinal Endoscopy* 38(3):338–340 (1992).

Liedberg et al., "Silver Coating of Urinary Catheters Prevents Adherence and Growth of Pseudomonas Aeruginosa" *Urol. Res.* 17:357–358 (1989).

Liedberg et al., "Assessment of Silver–Coated Urinary Catheter Toxicity by Cell Culture" *Urol. Res.* 17:359–360 (1989).

Mastrototaro et al., "Rigid and Flexible Thin–Film Multi–Electrode Arrays for Tansmural Cardiac Recording" *IEEE Transactions on Biomedical Engineering* 39(3):271–279 (1992).

Pyle et al., "Efficacy of Copper and Silver Ions with Iodine in the Inactivation of Pseudomonas Cepacia" *J. Appl. Bact.* 72:71–79 (1992).

Smoot et al., "In Vitro Toxicity Testing for Antibacterials Against Human Keratinocytes", *Plastics and Reconstructive Surgery* 87(5):917–924 (1991).

Swanson et al., "Surface Modification of Membranes for Medical and Industrial Applications" (Abstract), The 201st American Chemical Society National Meeting, Atlanta, GA, Apr. 14–19, 1991.

Tsai et al., "In Vitro Quantitative Study of Newly Made Antibacterial Braided Nylon Sutures" *Surgery, Gynecology & Obstetrics* 165:207–211 (1987).

Williams et al., "The Biocompatibility of Silver" *CRC Crit. Rev. Biocompat.* 5(3):221–243 (1989).

Zanoni et al., "A Comparison of Silver Nitrate with Erythromycin for Prophylaxis Against Ophthalmia Neonatorum" *Clinical Pediatrics* pp. 295–298 (1992).

Bio–Metrics Systems, Inc., "Photolink™ Surface Modification for Medical Devices", Technical Bulletin.

Bio–Metrics Systems, Inc., "Photolink™ Surface Modification and Immobilization Technology", Technical Bulletin, 1991.

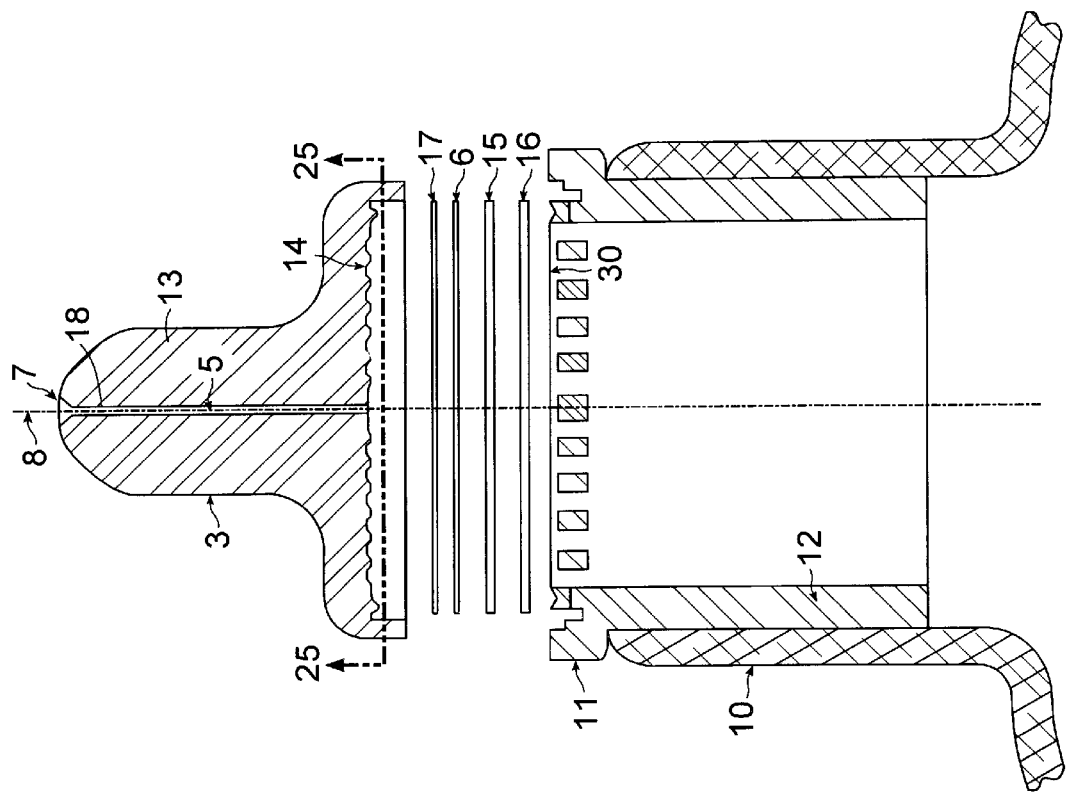
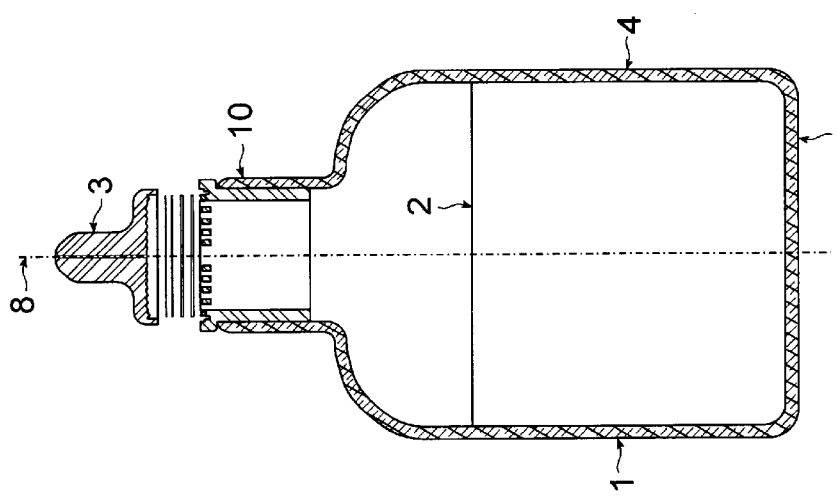

ANTIMICROBIAL LIQUID COMPOSITIONS AND METHODS FOR USING THEM

This application 371, filed Dec. 19, 1994, of International application no. PCT/US94/14636, which is c.i.p. of U.S. Ser. No. 08/220,821, filed Mar. 31, 1994 (now abandoned) which is a c.i.p. of U.S. Ser. No. 08/170,510, filed Dec. 20, 1993, (now issued as U.S. Pat. No. 5,490,938.

FIELD OF THE INVENTION

The present invention relates to liquid dispensers, specifically, the provision of liquid dispensers capable of maintaining the sterility of sterile solutions during storage, during dispensing, and subsequent to dispensing of the solution, as well as methods of manufacture and use of such dispensers.

BACKGROUND OF THE INVENTION

Many indications require administration of sterile solutions. In general, such solutions, and the dispensers in which they are stored, are sterilized prior to closure of the dispenser. Contamination can occur, however, after the dispenser is opened and used. Various approaches have been employed in attempts to minimize this contamination problem.

Single dose dispensers are available. Such dispensers, however, are made only for one time use, and then are discarded, adding considerably to packaging costs and waste. Moreover, more sterile solution than is required for a single dose usually is packaged which adds to the expense of the treatment. Another problem is that persons may attempt to use the single dose dispenser multiple times, which can result in contamination of the liquid being dispensed.

Alternatively, preservatives have been added to multi-dose dispensers to prevent microbial contamination after the dispenser is initially used. Such preservatives, however, often are toxic to mammalian cells, as well as microbial cells. For example, many preservatives used in eye drop formulations are toxic to the goblet cells in the eye. Such toxicity is detrimental to persons requiring prolonged application of the solutions. Moreover, persons often develop chemical sensitivity to the preservative, resulting in significant allergic reactions to the preparations. Such allergies can appear in some persons after prolonged exposure, as well as in others after only a single exposure.

Membrane filters have also been used in liquid dispensers in attempts to prevent microbial contamination of the stored sterile liquid. If a hydrophilic filter is used, however, the filter can allow the phenomenon known as "grow-through," in which microbial progeny on the downstream (non-sterile) side of the filter can pass through the filter pores because of their smaller size during cell division, and thereby contaminate the sterile solution contents in the dispenser.

Hydrophobic filters have been employed in liquid dispensers. Hydrophobic surfaces are non-wetting, and therefore are significantly more difficult for microbes to grow on. Such filters, however, because of their hydrophobicity prevent the flow of sterile aqueous solutions through the filter.

SUMMARY OF THE INVENTION

It is an object of the invention to provide a multi-dose liquid dispenser which prevents external microbial contamination of the liquid during repeated use.

According to the invention, an article of manufacture is provided—a liquid dispenser for dispensing a sterile liquid. The liquid dispenser comprises a container for storing the sterile liquid and a nozzle assembly which is attached to the container. The nozzle-assembly has a passageway which enables the sterile liquid to flow from the container through the passageway in order to dispense the liquid. The liquid dispenser further comprises an integral, non-leaching antimicrobial element for inhibiting microbial contamination of the solution. In one embodiment, the antimicrobial element comprises a filter or filters attached to the nozzle assembly and positioned across the passageway so that liquid and air flow are directed through the filter.

The filter comprises a substrate having an antimicrobial agent attached to the surface and in the pores thereof. The substrate may be an organic or inorganic material. The antimicrobial agent can be a metallic or non-metallic material having anti-bacterial, anti-viral and/or anti-fungal properties, or a combination thereof. In one embodiment, the filter is at least partially coated on the downstream surface with a metallic material, e.g., a metal, metal oxide, metal salt, metal complex, metal alloy, or mixtures thereof, which are bacteriostatic or bacteriocidal. The filter has pores of a size which precludes passage of microorganisms through the filter while permitting passage of the sterile liquid from the container through the filter. The pores are preferably approximately 0.1 microns to approximately 1.2 microns, and more preferably approximately 0.22 microns to approximately 0.65 microns in diameter.

In another embodiment, the upstream surface of the filter may be at least partially coated with the antimicrobial material.

In another embodiment, the surfaces and plurality of pores of the filter are at least partially coated with an additional different bacteriostatic or bacteriocidal material. A variation is the liquid dispenser having a second filter that is serially aligned with the first metal coated filter, and which is at least partially coated on at least one surface and within a plurality of its pores with a different bacteriostatic or bacteriocidal material.

In certain embodiments, the filter and a plurality of the pores can have at least a partial coating with a non-metallic antimicrobial compound that has an anti-viral, anti-fungal or anti-bacterial property. The non-metallic antimicrobial compound may be used in lieu of or in addition to the metallic materials.

In another embodiment, the filter includes a hydrophobic portion for allowing air to enter the container to replace the sterile liquid that is dispensed from the filter dispenser. In another variation, the dispenser may contain a second port separate from the dispensing nozzle for allowing replacement air into the container after the liquid is dispensed. In order to ensure the sterility of the air entering this second port, the port opening would be spanned by a hydrophobic membrane having a pore size that precludes bacterial migration into the dispenser, or having an antimicrobial agent attached thereto or coated thereon.

In yet another embodiment of the invention, the passageway walls in the nozzle assembly, at least on the downstream side of the filter, are coated with an antimicrobial material that is bacteriostatic or bacteriocidal. The antimicrobial material may be any of the metallic or non-metallic antimicrobial materials described herein.

In other variants, the liquid dispenser can have a prefilter which is spaced upstream from the filter for providing a barrier to the passage of particulate matter through the prefilter and for permitting the passage of sterile liquid from the container through the prefilter. A support means can also be spaced upstream from the filter for reinforcement of the filter.

In another embodiment of the present invention, the dispenser may contain an antimicrobial element in lieu of or in addition to the filter, the surface of which is at least partially coated with an antimicrobial agent. The element is disposed within the body of the container such that it remains in contact with the sterile solution at all times, e.g., during storage and dispensing. This is accomplished by providing a substrate having permanently attached thereto or coated thereon an antimicrobial agent. The substrate may be a bead or plurality of beads, a membrane, cartridge, filter, wool, cotton, baffle or fibrous bundle, for example. The element may be free-floating in the solution within the container or may be attached to or immobilized within the container. In this embodiment, the antimicrobial element remains in contact with the solution thereby insuring its sterility even after repeated doses have been dispensed by a user.

In another aspect of the above embodiment, the inside wall of the container which is in contact with the solution is coated with or has attached thereto an antimicrobial material.

Another aspect of the invention provides a membrane, element or surface which has an antimicrobial material coated thereon or attached thereto. In one embodiment, a microporous membrane having pores or other perforations which provide liquid conduits interconnecting the upstream and downstream surfaces of the membrane for liquid passage from one surface to the other is treated such that at least one surface and at least some of the pores are coated or otherwise derivatized with the antimicrobial material. The pores are of a size so as to preclude passage of microorganisms through the membrane and so as to permit passage of liquid and air through the membrane. Variations include all surfaces, including the pores, being at least partially coated with the antimicrobial material. The membrane surfaces and a plurality of the pores can be at least partially coated with an additional antimicrobial material that has an anti-viral, anti-fungal or anti-bacterial properties.

The invention also includes a method in which a liquid can be dispensed by applying pressure to the container of the liquid dispenser of this invention so as to discharge the liquid from the container. The container preferably is formed at least in part of a resiliently deformable material, such as an elastic polymer, which permits manual squeezing to discharge a dose of medicament, and subsequent elastic recovery of the material to its original configuration by drawing gas from a surrounding atmosphere into the container while the gas is sterilized by the filter in passing therethrough.

In a preferred embodiment of the invention, the liquid dispenser is used for eyecare in an individual, in which a sterile eyecare liquid, e.g., liquid artificial tears, a solution for contact lens care or a medicament, is dispensed from the liquid dispenser into the eye or onto an object that is to be placed into the eye. Preferably, the eyecare liquid is preservative-free.

The invention also features methods for attaching antimicrobial agents to the surfaces of a substrate. This may be accomplished by a number of methods. For example, metallic compounds may be applied to a surface by metal vapor deposition, electroless plating, chemical derivatization or coating. Non-metallic antimicrobial materials may be applied to such metallic surfaces by chemical derivatization or coating, for example.

In one embodiment, a metallic silver coating is accomplished by contacting the substrate with a carbonyl compound, e.g., an aldehyde such as glutaraldehyde, a sugar such as glucose, or an aldehyde functionality generating compound, drying the substrate, contacting the dried substrate with a metal salt, e.g., silver nitrate, or metal carboxylate salt solution, e.g., silver tartrate, and an amine-containing compound solution, e.g., ammonium hydroxide, so as to deposit the metal on the surface and within a plurality of the pores of the substrate. In an alternative embodiment, the drying step is omitted. One or more techniques may be combined to accomplish the desired result. For example, metal vapor deposition deposits metal on a surface of a membrane, but not in the pores. Therefore, antimicrobial material can be deposited in the pores of the membrane by an appropriate technique, followed by metal vapor deposition to coat the surface, thereby forming a membrane in which both the pores and the surface are coated with antimicrobial material.

In another embodiment, the substrate is contacted with an activator, e.g., a tin dichloride solution, is dried, and then contacted with a metal salt or metal carboxylate salt solution, either with or without an amine-containing compound solution, so as to deposit the metal on the surfaces of the substrate.

In another embodiment of the present invention, non-metallic antimicrobial agents are covalently attached to or coated onto a metal coated substrate such as a filter or an element disposed in the reservoir of the container. Non-metallic antimicrobial agents may include any anti-bacterial, anti-viral and/or anti-fungal materials which are capable of being immobilized on a surface and which are compatible with the sterile liquid. Most preferred are the class of agents which cause dissolution of the lipid bilayer membrane of a microorganism. For this purpose, surface active agents, compounds such as cationic or polycationic compounds, anionic or polyanionic compounds, non-ionic compounds and zwitterionic compounds may be used. Preferred agents include biguanide compounds or benzalkonium compounds. These agents may be attached to the substrate by covalent bonding, ionic interaction, coulombic interaction, hydrogen bonding, crosslinking (e.g., as crosslinked (cured) networks) or as interpenetrating networks, for example.

In another embodiment of the present invention, non-metallic antimicrobial agents are covalently attached to or coated onto a substrate such as a membrane, filter, an element disposed in the reservoir of the container or the walls of the reservoir in contact with the solution. These non-metallic agents are attached or coated directly onto the surface of the substrate in lieu of the metal coating. Non-metallic antimicrobial agents useful for his purpose include any anti-bacterial, anti-viral and/or anti-fungal materials which are capable of being immobilized on a surface and which are compatible with the liquid. Most preferred are the class of agents which cause dissolution of the lipid bilayer membrane of a microorganism. For this purpose, surface active agents, compounds such as cationic or polycationic compounds, anionic or polyanionic compounds, non-ionic compounds and zwitterionic compounds may be used. Preferred agents include biguanide compounds or benzalkonium compounds. These agents may be attached to the substrate by covalent bonding, ionic interaction, coulombic interaction, hydrogen bonding or interpenetrating networks, for example.

Articles made in accordance with these methods are also included in this invention.

A multidose dispenser containing a hydrophilic filter having immobilized thereon an antimicrobial agent that prevents bacterial grow-through while maintaining high flow rates of aqueous solutions was unknown in the art prior to Applicants' invention.

The present invention is unique in the following respects:

i) A multi-dose dispenser that incorporates a hydrophilic membrane which is surface modified (including pores) with a bound antimicrobial agent.

ii) The ability of the filter to prevent microbial grow through in long term contact applications, while maintaining high flow rates of aqueous solutions.

iii) The unique nature of the antimicrobial agent that utilizes a synergistic effect of it's components. This results in surface high biocidal activity, while maintaining almost no significant leachables into solutions it is in contact with iv) The mechanism of action being essentially a surface mediated one, whereby organisms succumb only upon contact with the filter due to the non leaching property associated with it.

v) The ability of such surfaces to remain viable over multiple organism challenges with no decrease in their bioactivity.

vi) The utilization of such biocidal coatings on the dispensing tip of the device, thereby eliminating the possibility of microbial colonization in the dead volume of the tip downstream to the filter.

vii) User friendliness and cost effectiveness of the device for all types of applications.

viii) Adaptability to existing manufacturing technology, thereby enabling large scale manufacture without added cost.

ix) Applicability to a variety of ophthalmic formulations over a wide range of solution viscosity including artificial tears, saline, anti-glaucoma and ocular hypertension drugs, and contact lens cleaning solutions.

x) Readily adaptable for varied flow requirements (single drop or stream).

xi) Readily adaptable for the delivery of other types of medicaments or solutions where preservatives have been used such as ear and nasal drug formulations.

The above and other objects, features and advantages of the present invention will be better understood from the following specification when read in conjunction with the accompanying drawings.

BRIEF DESCRIPTION OF THE DRAWINGS

FIG. 1 is a semi-diagrammatic cross-sectional view of a liquid dispenser in accordance with the present invention.

FIG. 2 is a semi-diagrammatic cross-sectional view of an upper portion of the liquid dispenser of FIG. 1.

DETAILED DESCRIPTION

Figure 3:
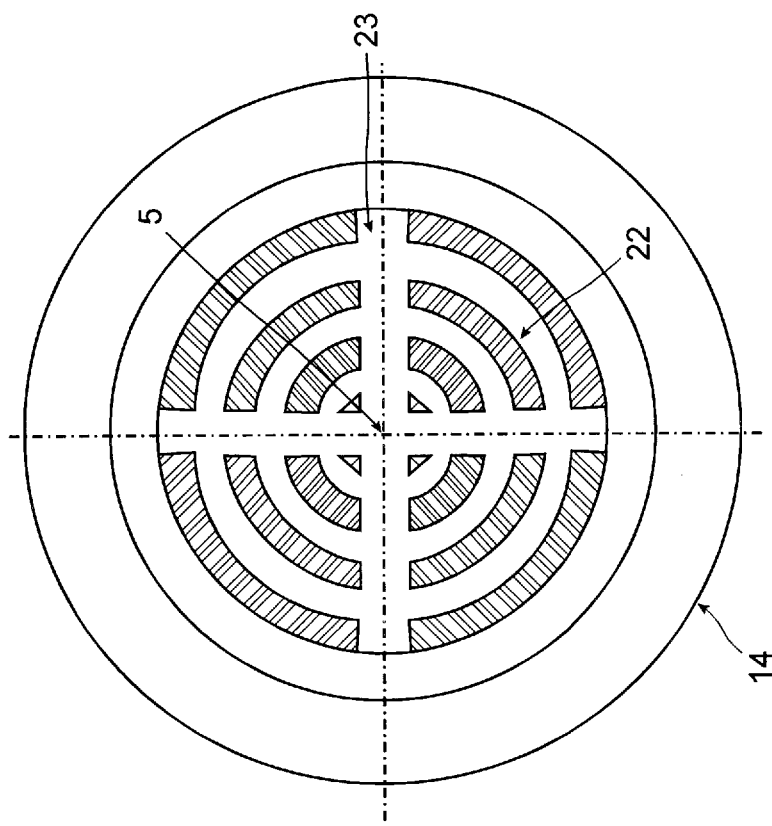
FIG. 3 is a semi-diagrammatic top view taken through line 25—25 of FIG. 2 showing the concentric and radial channels of the invention.

One embodiment of the present invention, as shown in FIGS. 1–3, provides a liquid dispenser 1 for dispensing a sterile liquid 2. The liquid dispenser 1 has a container 4 for storing sterile liquid 2 and a nozzle assembly 3 which is mounted on top of container 4. Nozzle assembly 3 has a passageway 5 which enables sterile liquid 2 to flow from container 4 through passageway 5 when sterile liquid 2 is dispensed.

Container 4 is designed to permit manual squeezing so as to force sterile liquid 2 from container 4 through filter 6 out of orifice 7 of nozzle assembly 3. In normal operation, liquid dispenser 1 is inverted and container 4 is squeezed.

Container 4, as shown in FIG. 1, has a circular cross-section extending along a vertical axis 8, with a flat bottom 9 and an upper end 10. Sidewall thickness is preferably in the range of 0.01 to 0.25 inch. However, various sizes and configurations can be used. The shape of the container can be round, elliptical, polygonal, irregular, or the like, and in some cases may be in tube form. The particular sidewall thickness can vary greatly, as can the volume of the chamber within container 4 that holds the medicament or other liquid to be dispensed. Thus, various sizes ranging from cubic millimeters to cubic centimeters or more can be used for the container chamber.

In a preferred embodiment, the nozzle assembly 3 is an ovoid form. The nozzle assembly has a cross-section formed of a plastic material which is self-supporting and defines a generally ovoid configuration having an inverted lip portion 11 mating with and sealed to the top of container 4 at upper end 10. Nozzle assembly 3 includes within it a ring-shaped lower spacer 12 of a solid material having a central passage connecting the chamber of container 4 with the filter or filters and an upper spacer 13 which acts to hold the filter or filters in place. The lower spacer 12 comprises a supporting screen 30. A disc 14 carries channel means. As shown in FIG. 3, disc 14 carries a plurality of concentric channels 22 which are interconnected by radial channels 23 to a central passageway 5 so that liquid coming from container 4 will pass through the filter or filters and be distributed on the surface of disc 14 so as to cause dispensed sterile liquid 2 to coalesce into a single drop or a stream of liquid when expelled from container 4. Depending on factors including, e.g., the applied pressure, the viscosity of the expelled liquid and the surface area of disc 14, either a single drop or a stream of liquid will be dispensed. Disc 14 is held in place by being adhesively secured, e.g., by ultrasonic welding or by a mechanical force, to the upper spacer 13. Support 16, prefilter 15, filter 6 and second filter 17 can be suspended by spacers 12 and 13. In some embodiments, only filter 6 need be used and one or more of the support, prefilter or second filter, can be eliminated. Various combinations of these elements can be used in different embodiments as desired.

While the prefilter and filter, as well as the second filter, are shown as planar members, various configurations can be used. These members can be in the form of cones, polygonal or other shaped devices as may be desirable for specific applications. Planar sheet-type materials as shown are most preferred.

While passageway 5 is preferably axially extending with a circular cross-section, it can have any configuration as desired for specific applications.

Container 4 can be formed from a flexible material; e.g., an elastically deformable polymer which may be a thermosetting or thermoplastic polymeric material, including, for example, polypropylene, polyethylene, polyvinylchloride, polyethylene terephthalate, polytetrafluoroethylene, polysulfone and polyethersulfone polymers or copolymers. In some cases the container can be a deformable metallic or plastic medicament container, such as a toothpaste tube, where the container may remain deformed after each dose is dispensed.

Nozzle assembly 3 can be formed from the same or a more rigid type of material than container 4. In one embodiment, nozzle assembly 3 is permanently attached to container 4 with a liquid-tight connection so as to aid in maintaining the sterility of sterile liquid 2 in container 4. Such a connection can be formed by standard techniques, e.g., ultrasonic welding, heat press sealing, adhesive sealing or mechanical sealing.

Filter 6 is sealingly attached to nozzle assembly 3 so that filter 6 extends across the entire expanse of passageway 5 to direct liquid and air flow out of and into containers through filter 6. Filter 6 can be attached to nozzle assembly 3 by any method which results in such a seal, including, e.g., ultrasonic sealing, heat press sealing and adhesive sealing.

By filter is meant any material which can function as a microbial filter. Microporous membranes are preferred filter materials. As used herein, the term "microporous" means having pores of an average diameter of 5 m or less. Membranes used in the filter of this invention may be formed from organic or inorganic materials. Organic materials include polymeric materials which can be used for the preparation of membranes or filter papers. Examples of organic polymeric materials include polysulfone, polyethersulfone, polyamide (e.g., nylon), polycarbonate, polyacrylate, polyvinylidene fluoride, polyethylene, polypropylene, cellulosics (e.g., cellulose), and Teflon®. The hydrophobic materials, e.g., polypropylene or Teflon®, may require prior surface activation with techniques such as plasma, chemical oxidation or metallic sensitization, e.g., a primer. Inorganic filters include glass fiber filter paper, ceramic membranes (e.g., alumina or silica), and metal filters. Sintered glass and sintered ceramic blocks also can be used. The filters can be either hydrophilic or hydrophobic. If a hydrophobic filter is used, the metal coating, described below, converts it to a filter with hydrophilic properties.

Filter 6 has pores which form interconnecting liquid conduits extending from an upstream surface of the filter to a downstream surface. The pore size for filter 6 is chosen so that the pores permit passage of sterile liquid 2 from container 4 through filter 6, but preclude passage of microorganisms through filter 6, thereby maintaining the sterility of sterile liquid 2 in container 4. By microorganism is meant bacteria, blue-green algae, fungi, yeast, mycoplasmids, protozoa and algae. The pore size can range from approximately 0.1 microns to approximately 1.2 microns. Preferably, the pore size is approximately 0.22 microns to approximately 0.65 microns. Most preferably, the pore size is about 0.65 microns. Whereas 0.22 microns is the pore size used in most bacterial filtration systems, this invention can produce a sterile filtrate with larger pore sizes, e.g., 0.45 and 0.65 microns, thus permitting a device which gives a faster flow rate for the dispensed liquid.

A major problem in multi-dose liquid dispensers is that residual liquid may accumulate downstream of the filter subsequent to dispensing liquid from the container. By downstream of the filter is meant the side of the filter that liquid from the container which has passed through the filter would be on, e.g., the surface of the filter exposed to the outside atmosphere. By upstream of the filter is meant the side of the filter facing the liquid in the container which has not yet passed through the filter. Microorganisms can multiply in this accumulated downstream liquid and contaminate liquid which is subsequently dispensed. Moreover, certain microorganisms in this accumulated liquid can, because of their smaller size during cell division, pass through the pores of the filter, a phenomenon known as "grow-through," and contaminate the sterile liquid in the container.

This invention addresses this problem by providing that filter 6 be at least partially coated with or has attached thereto on the downstream surface and within a plurality of the pores with an antimicrobial material that is bacteriostatic or bacteriocidal. By bacteriocidal is meant the killing of microorganisms. By bacteriostatic is meant inhibiting the growth of microorganisms, which can be reversible under certain conditions. The antimicrobial agent may be a metal or metal compound, a non-metallic compound, or a combination of both.

In a preferred embodiment, the antimicrobial agent is a metal, metal oxide, metal salt, metal complex, metal alloy or mixture thereof which is bacteriocidal or bacteriostatic. By a metallic material that is bacteriostatic or bacteriocidal is meant a metallic material that is bacteriostatic to a microorganism, or that is bacteriocidal to a microorganism, or that is bacteriocidal to certain microorganisms and bacteriostatic to other microorganisms. In certain embodiments, filter 6 is also at least partially coated on the upstream surface with a metallic material, e.g., a metal, metal oxide, metal salt, metal complex or metal alloy or mixtures thereof. Any metal which is bacteriostatic or bacteriocidal can be used. Examples of such metals include, e.g., silver, zinc, cadmium, mercury, antimony, gold, aluminum, copper, platinum and palladium. The appropriate metal coating is chosen based upon the use to which the sterile liquid passing over the metal coated filter is to be put. Preferably, metals which are not toxic are attached to filters which are to be used for filtering solutions that are to be applied to humans and other organisms. The currently preferred metal is silver.

In another embodiment of the present invention, filter 6 is first coated with an antimicrobial metal, metal salt or metal complex material, and a non-metallic antimicrobial agent is covalently attached to or coated onto the metal coated substrate. Non-metallic antimicrobial agents useful for this purpose include any anti-bacterial, anti-viral and/or anti-fungal materials which are capable of being immobilized on a surface and which are compatible with the sterile liquid. Most preferred are the class of agents which cause dissolution of the lipid bilayer membrane of a microorganism. For this purpose, surface active agents, compounds such as cationic or polycationic compounds, anionic or polyanionic compounds, non-ionic compounds and zwitterionic compounds may be used. Preferred agents include biguanide compounds or benzalkonium compounds. These agents may be attached to the substrate by covalent bonding, ionic interaction, coulombic interaction, hydrogen bonding, crosslinking (e.g., as crosslinked (cured) networks) or as interpenetrating networks, for example.

In another embodiment of the present invention, filter 6 is treated with non-metallic antimicrobial agents which are covalently attached to or coated onto the surfaces and/or pores of the filter. These non-metallic agents are attached or coated directly onto the surface and/or pores of the substrate in lieu of the metal coating. Non-metallic antimicrobial agents useful for his purpose include any anti-bacterial, anti-viral and/or anti-fungal materials which are capable of being immobilized on a surface and which are compatible with the liquid. Most preferred are the class of agents which cause dissolution of the lipid bilayer membrane of a microorganism. For this purpose, surface active agents, compounds such as cationic or polycationic compounds, anionic or polyanionic compounds, non-ionic compounds and zwitterionic compounds may be used. Preferred agents include biguanide compounds or benzalkonium compounds. These agents may be attached to the substrate by covalent bonding, ionic interaction, coulombic interaction, hydrogen bonding, crossinking (e.g, as crosslinked (cured) networks) or as interpenetrating networks, for example.

In another embodiment of the present invention, filter 6 is treated with non-metallic antimicrobial agents which are covalently attached to or coated onto the surfaces and/or pores of the filter. These non-metallic agents are attached or coated directly onto the surface and/or pores of the substrate. Non-metallic antimicrobial agents useful for this purpose include any anti-bacterial, anti-viral and/or anti-fungal materials which are capable of being immobilized on a surface and which are compatible with the liquid. Most preferred are the class of agents which cause dissolution of the lipid bilayer membrane of a microorganism. For this purpose, surface active agents, compounds such as cationic or polycationic compounds, anionic or polyanionic compounds, non-ionic compounds and zwitterionic compounds may be used. Preferred agents include biguanide compounds or benzalkonium compounds. These agents may be attached to the substrate by covalent bonding, ionic interaction, coulombic interaction, hydrogen bonding, crosslinking (e.g. as crosslinked (cured) networks) or as interpenetrating networks, for example. An antimicrobial metal, metal salt or metal complex material is introduced into the non-metallic antimicrobial coating either prior to or after coating the surface in the form of either as particles or as a homogeneous solution.

In one embodiment, filter 6 is a membrane having both hydrophilic and hydrophobic regions. For example, a hydrophobic filter which has only been coated with a metal or metal oxide or metal salt on a portion of the filter, will be hydrophilic for the coated portion and hydrophobic for the uncoated portion. In another example, a hydrophilic or hydrophobic filter is coated with a metal, metal oxide or metal salt, so as to make the filter hydrophilic, and then a portion of this metallic surface is rendered hydrophobic by incorporation of a hydrophobic coating via formation of a spontaneously self-assembled monolayer that is covalently attached to the metallic surface, e.g., formation of an alkyl thiolate monolayer on a silver coated surface by treatment with a solution of an alkyl thiol, such as dodecane thiol. In another example, a portion of a hydrophilic filter may be rendered hydrophobic by treatment with a polymeric siloxane, a perfluoro polymer, or silyl monomer(s) or perfluoro monomer(s) that may be polymerized thermally, photolytically or chemically. Such a dual purpose filter is preferred when multiple doses of liquid are dispensed in quick succession to each other, in order to more quickly replace the liquid which has been dispensed from the container with air from outside the container, so as to equalize the pressure. The dispensed liquid can pass through the hydrophilic portion of the filter, and the replacement air can pass through the hydrophobic portion without being hampered by the presence of liquid on the hydrophilic portion.

In the embodiment of FIG. 2, an air port or vent (not shown) can be provided through upper spacer 13 positioned directly above the hydrophobic portion of the filter so as to allow air passage to container 4 as the liquid is dispensed from container 4. The air port or vent provides for compensation of the air pressure as liquid is dispensed from the container so as to avoid formation of a vacuum. The device will work with or without the air port or vent, however, if a constant and sustained flow is desired, better flow rates may be obtained with the use of an air port or vent. In those cases where a hydrophobic/hydrophilic membrane is used, the air port or vent described may be particularly desirable to equalize pressure as liquids leave the container. In such a case, it is preferred that the air port or vent be positioned above the hydrophobic portion of the filter.

The invention also provides for a filter in which the downstream surface and a plurality of the pores are at least partially coated with an additional second antimicrobial material. In one embodiment, the upstream surface is also at least partially coated with a second metal, metal oxide, metal salt, metal complex or metal alloy, or mixture thereof. Examples of metals that can be used are discussed above in relation to the single metal coating. The use of two different metals can enhance the antimicrobial properties of the filter. Different types of microorganisms can exhibit different degrees of sensitivity to different metals. In addition, the use of two different metals can significantly reduce the problem of selection for microorganisms having resistance to the metal in the metal coating that can occur when only one metal is used.

Another variation of the invention is a liquid dispenser which has a second filter 17 with pores of a size that permits passage of sterile liquid 2 from container 4, that is serially aligned with filter 6. Second filter 17 is at least partially coated on at least one surface and within a plurality of its pores with a different antimicrobial material, e.g., a metal, metal oxide, metal salt, metal complex or metal alloy or mixtures thereof, that is bacteriostatic or bacteriocidal, than is used for the coating on filter 6. The presence of different antimicrobial materials on different filters in the liquid dispenser is advantageous for the same reasons as discussed above regarding the embodiment where two different antimicrobial materials are applied to a single filter. In other embodiments, more than two different antimicrobial filters are present.

In another embodiment of this invention, the surfaces of the filter (or other membrane) and a plurality of pores of the filter or membrane is coated with or has attached thereto, a non-metallic compound that has antimicrobial properties, e.g., antiviral, antibacterial and/or antifungal properties. By anti-viral is meant capable of killing, or suppressing the replication of, viruses. By anti-bacterial is meant bacteriostatic or bacteriocidal. By antifungal is meant capable of killing or suppressing replication of fungi. This non-metallic antimicrobial material may be used in lieu of or in addition to the metallic coating. Use of these materials in conjunction with the metallic agent as an additional coating can allow for more effective anti-bacterial liquid dispensers, in that different anti-bacterial compounds can exhibit different degrees of effectiveness for different types of microorganisms. Multiple anti-bacterial compounds also significantly reduce the problem of selection for microorganisms having resistance to the metal in the metal coating, as discussed above. Moreover, a combination of antimicrobial materials can allow for joint anti-bacterial/anti-viral/anti-fungal liquid dispensers. Preferably, this compound is bound to at least a portion of the first antimicrobial coating on the filter. Any compound which has anti-bacterial, anti-fungal or anti-viral activity can be used. Examples of such compounds include cationic or polycationic compounds, anionic or polyanionic compounds, non-ionic compounds and zwitterionic compounds. Preferred compounds include benzalkoniumchloride derivatives (see, for example, Example 9), a-4-[1-tris (2-hydroxyethyl) ammonium-2-butenyl]poly[1- dimethylammonium-2-butenyl]-ω-tris(2-hydroxyethyl) ammonium chloride, and biguanides of the general formula:

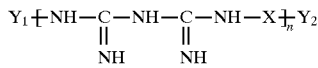

or their water soluble salts, where X is any aliphatic, cycloaliphatic, aromatic, substituted aliphatic, substituted aromatic, heteroaliphatic, heterocyclic, or heteroaromatic compound, or a mixture of any of these, and $Y_1$ and $Y_2$ are any aliphatic, cycloaliphatic, aromatic, substituted aliphatic, substituted aromatic, heteroaliphatic, heterocyclic, or heteroaromatic compound, or a mixture of any of these, and where n is an integer equal to or greater than 1. Preferred compounds include, e.g., chlorhexidine or polyhexamethylene biguanide (both available from Zeneca of Wilmington, Del.). These compounds may be modified to include a thiol group in their structure so as to allow for the bonding of the compound to the metallic surface of the filter. Alternatively, these compounds may be derivatized with other functional groups to permit direct immobilization on a non-metallic surface. For example, the above-mentioned antimicrobials may be suitably functionalized to incorporate groups such as hydroxy, amine, halogen, epoxy, alkyl or alkoxy silyl functionalities to enable direct immobilization to the surface in lieu of a metal.

Antimicrobial elements having the various antimicrobial compounds coated or attached thereon described above also are included in this invention.

The invention also includes an embodiment in which the liquid dispenser has a prefilter 15 which is spaced upstream from filter 6 and provides a barrier to the passage of particulate matter through prefilter 15, while permitting passage of sterile liquid 2 from container 4 through prefilter 15. In this manner, particulate matter that may be present in sterile liquid 2 in container 4 does not need to be filtered by filter 6, and thus prevents clogging of filter 6, thereby aiding in preserving the capacity of, and flow rate through, filter 6. Preferably, the pore size of prefilter 15 is approximately 1 micron to approximately 50 microns. The prefilter material includes, e.g., glass fibers, synthetic polymer fibers, e.g., hydrophilic polypropylene fibers, nylon and cellulosic fibers. Preferably, prefilter 15 is attached to filter 6 in embodiments where there is only one filter, or attached to the most upstream filter where there is more than one filter, and is also attached to nozzle assembly 3. Preferably, the attachments are by welding.

In another embodiment, the liquid dispenser has a support 16 which is spaced upstream from the filter to act as a reinforcement for the filter. Preferably, support 16 is perforated. Support 16 can be made from any material that the container or nozzle assembly is made from.

In other embodiments of the invention, the internal walls 18 of nozzle assembly 3 are at least partially coated, with an antimicrobial agent As described herein above, the agent may be a metallic material, e.g., a metal, metal oxide, metal salt, metal complex, metal alloy or mixtures thereof, or may be a non-metallic organic material that is bacteriostatic or bacteriocidal or a combination of the two. After the liquid dispenser of the invention has initially been used to dispense liquid from container 4, some residual liquid may remain on internal walls 18 of nozzle assembly 3 downstream from filter 6. Microorganisms can grow in this residual liquid and contaminate any future drops of liquid which are dispensed. By coating these walls with an anti-bacterial material, this contamination is reduced. Examples of metals and non-metallic materials which can be used to coat the nozzle assembly walls were discussed above in relation to coating filter 6. Example 12 describes a method for depositing silver onto the walls of the nozzle assembly.

Figure 5:
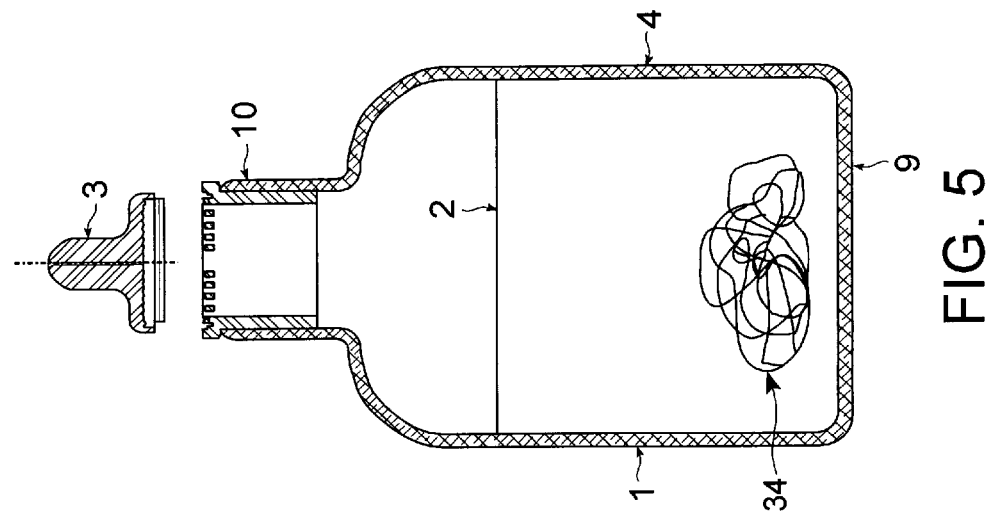
FIG. 5 is a semi-diagrammatic cross-sectional view of a liquid dispenser of FIG. 4 containing antimicrobial coated fibers.
Figure 4:
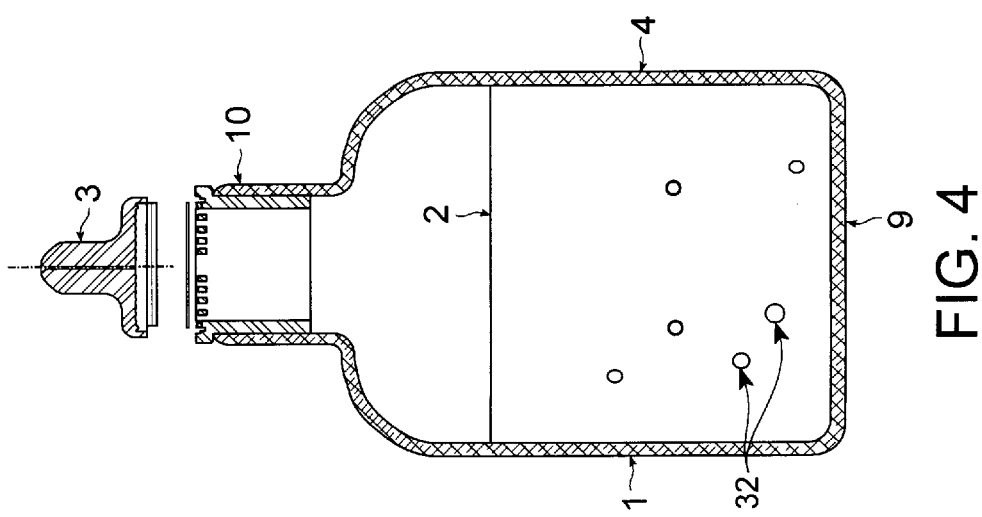
FIG. 4 is a semi-diagrammatic cross-sectional view of a liquid dispenser containing anti-microbial coated beads in accordance with the present invention.

In another preferred embodiment, shown in FIGS. 4–5, the container 4 has disposed therein an antimicrobial element in contact with sterile liquid 2. In this embodiment, the antimicrobial element may be present in lieu of or in addition to the filter. The element comprises an organic or inorganic substrate having an antimicrobial agent attached thereto as coated thereon. The substrate may have any shape or configuration and may be free-floating within the container or may be attached to or be an integral part of the container. In the embodiment shown in FIG. 4, the substrate comprises beads 32. In the embodiment shown in FIG. 5, the substrate comprises a cotton ball 34. Other substrate configurations including cartridges, fibrous bundles, membranes or baffles may be used. The substrate may be formed from any material compatible with the sterile liquid, for example, plastic, metal or cellulosic material. The substrate preferably is inert and non-degradable in the sterile liquid. The currently preferred materials for use as a substrate include glass or polymeric beads or pellets, fibers and non-woven materials such as cotton or cellulose, or metal foils. The preferred substrate will be antimicrobial, either naturally or will have attached thereto or coated thereon an antimicrobial agent. Examples of naturally antimicrobial materials include certain metals, metal oxides, metal salts, metal complexes and metal alloys. For example, a metal foil such as silver foil may be used. Substrates which are not anti-microbial have immobilized thereon an antimicrobial agent. Antimicrobial agents which may be used include the metallic and non-metallic agents discussed in detail herein.

The amount and/or type of the antimicrobial agent which is used in a particular application will vary depending on several factors, including the amount of liquid which must be maintained in a sterile environment, the type and amount of contamination which is likely to occur, and the size of the antimicrobial surface present in the dispenser or other container. For example, certain metals, such as silver, are highly effective against most bacteria, but less effective against yeast (such as *Candida albicans*). However, non-metallic agents such as biguanide compounds, are toxic to yeast. Therefore, if the sterile liquid is likely to be exposed to contamination by both bacteria and yeast, a combination of silver and a biguanide compound can be used as the antimicrobial. The amount of antimicrobial used will be a minimum amount necessary to maintain the sterility of the liquid. As stated above, this amount will vary depending upon various considerations.

In a preferred embodiment, glass beads coated with metallic silver or a silver salt are added to the sterile liquid. The silver compound is attached to the beads such that the silver is substantially non-leachable. As used herein, the term "substantially "non-leachable" means that none or very small amounts (e.g., below a certain threshold) of the non-leachable material dissolves into the sterile liquid. It is understood that minute amounts of silver or other antimicrobial agent may dissolve into the solution, but these amounts are minute. The amount of dissolved silver in the sterile liquid may be substantially reduced by passivating the silver coated surface by reaction with compounds which form silver salts or salt complexes. For example, reaction with halogens, e.g., chlorine, iodine, bromine or mixtures thereof may be performed, thereby generating a layer of silver halide on the metallic silver coating. Other embodiments include, for example, pellets or beads formed from an inert polymeric material, such as polyethersulfone, having an an organic, inorganic or a combination of the two types of antimicrobial agents attached or coated on the surface. Preferred inorganic antimicrobial agents include elemental silver or silver compounds. Preferred organic antimicrobial agents include cationic or polycationic compounds, anionic or polyanionic compounds, non-ionic compounds and zwitterionic compounds. Preferred compounds include benzalkonium chloride derivatives and biguanide compounds, all of which are discussed in detail hereinabove.

In methods of the invention the surfaces and pores of a filter or other substrate are coated with a metallic or non-metallic antimicrobial compound, or a combination of the two types. In one embodiment, a filter having pores is provided, the filter is contacted with a carbonyl compound, the filter is dried, and the dried filter is contacted with a metal salt solution or metal carboxylate salt solution and an amine-containing compound solution so as to deposit the metal on the surface and within a plurality of the pores. In one embodiment, this filter is then washed and dried. Other elements such as glass or polymeric beads, glass wool, glass or polymeric fibers, membranes, cotton or other fibrous material or cartridges etc. can be treated in like manner to coat or attach an antimicrobial agent.

The carbonyl compound includes, e.g., aldehydes, sugars, and aldehyde functionality generating compounds. Aldehydes include compounds with the formula $R(CHO)_n$, where R is any aliphatic, aromatic or heteroaromatic group and n is an integer greater or equal to 1. Examples of water soluble aldehydes are glutaraldehyde, formaldehyde, acetaldehyde, butyraldehyde, glyceraldehyde, glyoxal, glyoxal disodium bisulfite, paraldehyde and cyclic trioxanes. Examples of water insoluble aldehydes are cinnamaldehyde and benzaldehyde. By sugar is meant a reducing sugar. Sugars include, e.g., fructose, glucose, lactose, maltose and galactose. By an aldehyde functionality generating compound it is meant a compound capable of generating aldehyde group(s). Examples of such compounds include acetals and hemiacetals. Polymeric acetals, e.g., paraformaldehyde and polyacetal, can also be used in this invention. The carbonyl compound acts as a reducing agent, so that the metal ion is reduced to the metal, e.g., silver ion is reduced to metallic silver. This electroless redox reaction occurs in situ in solution or in the solid state. The carbonyl compound has affinity for aqueous and non-aqueous phases and therefore can be used in the process of coating either hydrophilic or hydrophobic filters. If hydrophobic filters are used, the resulting metal coating confers hydrophilic properties on the coated filter.

After treatment with the carbonyl compound, the filter or other substrate is either immersed directly into the metal salt solution or metal carboxylate salt solution, or is dried first and then immersed in this solution. Preferably, the filter is first dried. The drying step increases the metal coating within the pores of the filter and produces a more uniform and adhesive metal coating thickness on the surface and within the pores of the filter. Coating within the pores enhances the bacteriostatic or bacteriocidal properties of the filters.

Any metal which has bacteriostatic or bacteriocidal properties, as described above, can be used in this invention to coat the substrate. In a preferred embodiment, the metal is silver. The silver salts that can be used in the metal coating process are salts that are capable of solubilizing, even to a limited degree, in aqueous media, to produce silver ions. Such salts include, e.g., silver nitrate, silver benzoate, silver tartrate and silver acetate, silver citrate or any silver carboxylate.

Metal carboxylate salts include compounds with the formula $R(COO^-M^+)_n$, where R is any aliphatic, aromatic or heteroaromatic group and n is an integer greater or equal to 1. Examples of metal carboxylate salts include, e.g., silver, zinc, cadmium, mercury, antimony, gold, aluminum, copper, platinum and palladium salts of acetic, propanoic, lactic or benzoic acid; and mono- or di- sodium or potassium salts of diacids, e.g., oxalic, malonic, glutaric or tartaric acids. The term metal carboxylate salts is also meant to include carboxylic acids which are capable of forming carboxylate salts in situ under conditions including the presence of a base and a metal ion, and compounds which are capable of forming carboxylic or carboxylate groups in situ, including, e.g., esters, lactones, anhydrides and amides.

By amine-containing compound it is meant a compound capable of producing a metal-amine complex when metal salts react with amines under basic conditions. Examples of amine-containing compounds include ammonium hydroxide, ammonia, and aliphatic, aromatic and heteroaromatic amines.

In another embodiment, a filter having pores is provided, the filter is contacted with an activator, the filter is dried, and the dried filter is contacted with a metal salt or metal carboxylate salt solution so as to deposit the metal on the surface and within a plurality of the pores of the filter. The activator is a salt of a metal including, e.g., tin, titanium, vanadium, chromium, manganese, iron, cobalt, nickel, copper, zinc, germanium, selenium, zirconium, niobium, molybdenum, technetium, ruthenium, rhodium, palladium, antimony, tellurium and lead. A preferred activator is tin dichloride. An alternative embodiment is to contact the dried filter with an amine containing compound in addition to the metal salt or metal carboxylate salt solution.

Additionally, many types of metals can be plated onto the surface of suitably primed polymeric materials using standard well known electroplating techniques or by electroless methods. It is necessary to prime the polymer surface to allow for the electroplating process to occur because most polymers are electrically insulating and do not carry an electrical current. Priming deposits a very small amount of metal onto the surface of the polymer allowing for the subsequent electrolytic deposition of a metal from solution.

The metal coating on the filters derived from any of the methods discussed above, can be further treated to produce a metal oxide coating, as described in Example 8, or a metal halide coating, as described in Example 16.

The invention further provides methods for attaching or coating non-metallic antimicrobial agents to a surface. In this embodiment antimicrobial agents including the anti-bacterial, anti-viral and/or anti-fungal agents described herein are non-leachably immobilized on the surface of a filter or other element. These non-metallic agents may be used in lieu of or in addition to the metallic antimicrobial agents. The non-metallic agents may be immobilized by any suitable method, including covalent bonding, ionic attraction, coulombic interaction, hydrogen bonding and interpenetrating networks, for example. Methods for attaching organic antimicrobial agents to a metal surface are described in Examples 16 and 17.

The invention further provides methods for attaching or coating a combination of a metallic and non-metallic antimicrobial agents to a surface. In this embodiment antimicrobial agents including the anti-bacterial, anti-viral and/or anti-fungal agents described herein are non-leachably immobilized on the surface of a filter or other element. The non-metallic agents may be immobilized by any suitable method, including covalent bonding, ionic attraction, coulombic interaction, hydrogen bonding, cross-linking (curing) and interpenetrating networks, for example. The metallic antimicrobial may be introduced in the non metallic antimicrobial coating either prior to or after applying the coating to the surface. The metallic antimicrobial may consist of a metal, metal salt or metal complex may be introduced into the non-metallic antimicrobial either as particles or as a homogeneous solution. Methods for attaching organic antimicrobial agents to a metal surface are described in Examples 16 and 17.

The substrate may be pretreated, if necessary, to activate the surface. In one embodiment, the surface is silylated to render it more receptive to binding antimicrobial agents. Silylation can be carried out by art-recognized techniques including direct coupling reactions, grafting reactions and dendrimer-type reactions. The antimicrobial agent then is reacted with the resulting silyl functionality, or to a group attached to the silyl functionality. Methods for immobilizing antimicrobial compounds on silylated surfaces are described in Example 17.

In another embodiment, metallic and non-metallic antimicrobial agents may be attached to non-silylated surfaces. In this embodiment, the surface is treated to obtain carboxylic or amine functionalities as described above, and the antimicrobial agent is attached by reaction with these functionalities. Methods for immobilizing antimicrobial materials on a non-silylated surface are described in Example 18.

This invention also includes the products made in accordance with these methods.

This invention also provides a method for dispensing sterile liquid by applying pressure to the container of the liquid dispenser of this invention so as to discharge the sterile liquid from the container. In one embodiment, the container has an elastically deformable wall, pressure is applied to deform the wall and force the sterile liquid from the container through the filter, and the wall is allowed to recover so as to draw gas from the surrounding atmosphere into the container, the gas being sterilized as it passes through the filter.

The liquid dispenser can be used for any purpose which requires dispensing a sterile solution from a container. Such uses include, e.g., medical related purposes, e.g., dispensing sterile liquids onto any part of the body of an organism or onto an object that is to be placed into the body of an organism, e.g, for use in eye, ear, or nose care. For example, this invention provides a method for using the liquid dispenser of this invention for eyecare in an organism in which a sterile eyecare liquid is dispensed into an eye of the organism or onto an object that is to be placed into the eye of the organism. Preferably, the sterile eyecare liquid is preservative-free. The sterile eyecare liquid includes, e.g., liquid artificial tears, a solution for contact lens care or a medicament. Examples of medicaments are antibiotics, decongestants, anti-inflammatories, anti-glaucoma agents, anti-bacterial agents, anti-viral agents, anesthetics, mydriatics, anti-cholingerics and miotics. An object that is to be placed into the eye includes, e.g., a contact lens. Other uses include process filters for sterilization of all types of solutions, e.g., drug solutions and instillation solutions; intravenous catheters, where a membrane unit is employed for the admittance of air but prevents back flow of blood or other liquids; process filters for food products where sterility is required; dispensation of items such as baby formula where the presence of a preservative would be undesirable; and membrane filter units, e.g., for campers and hikers where the generation of microbial free water is desired without the possibility of future contamination.

EXAMPLES

Example 1

Metal Vapor Deposition (MVD) of Silver Onto a Polyethersulfone Membrane

This example illustrates a method for depositing silver onto a surface, but not within the pores, of a membrane filter. A precut polyethersulfone membrane (Supor 450, pore size 0.45 4M, hydrophilic, obtained from Gelman of Ann Arbor, Mich.) was mounted on a plate such that the surface to be coated faced the heating source of a metal evaporator. An approximately 4–6 inch long silver wire (obtained from Johnson Matthey of Wardhill, Mass.) was rolled into a coil and placed on the metal bridge in the evaporator. The evaporator was pumped down to $10^{-5}$ Torr and a current of approximately 60–70 amperes was applied to melt the silver. A uniform silver coating of the membrane surface resulted in about 15–30 secs. The current was turned off and the evaporator chamber was allowed to return to atmospheric pressure. The membrane was turned over and the procedure repeated. The resulting membrane had a uniform coating of silver on both surfaces, but not within the pores, as determined by scanning electron microscopy (SEM) and energy dispersive X-ray analysis (EDAX).

Example 2

Electroless Coating of Silver Onto a Polyethersulfone Membrane (Method 1)

This example illustrates a method for depositing metallic silver onto a surface, and within the pores, of a membrane filter. A polyethersulfone membrane Gelman Supor 450, pore size 0.45 mM, hydrophilic) was precut into a 47 mm disk. This membrane was immersed in 5 ml of glutaraldehyde (25% solution, obtained from Aldrich of Milwaukee, Wis.) for 1 min. at 22° C., removed from the aldehyde solution and air dried thoroughly. The treated membrane was then immersed in 5 ml of the silver coating solution described in Example 7A, at pH approximately 12 (the pH can range from approximately 8–14), at 35° C. for 15 secs. The plated membrane was thoroughly rinsed with distilled water and dried in a vacuum oven at 20° C. for 2 hrs. SEM coupled with EDAX showed uniform silver coating on the membrane surface and within the pores. (Ag:S=0.4–0.5:1)

Example 3

Electroless Coating of Silver Onto a Polyethersulfone Membrane (Method 2)

This example illustrates a method for depositing metallic silver onto a surface and within the pores of a membrane filter. A polyethersulfone membrane (Millipore, pore size 0.45 mM, hydrophobic, obtained from Millipore Corp. of Bedford, Mass.), was precut into a 47 mm disk. This membrane was immersed in 5 ml of 0.1M a-D-glucose in an aqueous solution containing 10% ethanol for 5 mins. at 22° C., removed from the sugar solution and air dried thoroughly. The treated membrane was then immersed in 5 ml of the silver coating solution described in Example 7A, at pH approximately 12 at 35° C. for 2 mins. The plated membrane was thoroughly rinsed with distilled water and dried in a vacuum oven at 20° C. for 2 hrs. SEM coupled with EDAX showed uniform silver coating on the membrane surface and within the pores. (Ag:S=0.8:1)

Example 4

Electroless Coating of Silver Onto a Polyethersulfone Membrane (Method 3)

A polyethersulfone membrane (Gelman, pore size 0.45 mM, hydrophilic) was precut in the form of a 47 mm disk. This was immersed in 5 ml of a 0.1M a-D-glucose in an aqueous solution containing 10% ethanol for 5 minutes at 22 deg. C. It was then removed from the sugar solution and air dried thoroughly. The treated membrane was then immersed in 5 ml of a silver plating solution 1 (pH ~12) at 35 deg. C. for 2 minutes. A rapid deposition of metallic silver on the membrane surface ensued. The plated membrane was thoroughly rinsed with distilled water and dried in a vacuum oven at 20 deg. C. for 12 hours. SEM coupled with EDAX showed uniform silver coating on the membrane surface and within the pores. (Ag:S=0.3:1)

Example 5

Electroless Coating of Silver Onto a Polyethersulfone Membrane (Method 4)

This example illustrates a method for depositing metallic silver onto a surface and within the pores of a membrane filter. A polyethersulfone membrane (Gelman Supor 450, pore size 0.45 mM, hydrophilic) was precut into a 47 mm disk. This membrane was immersed in 5 ml of the silver coating solution described in Example 7B, which was then heated to 55° C. and maintained at this temperature for 5 mins. Rapid deposition of metallic silver onto the membrane ensued. The plated membrane was thoroughly rinsed with distilled water and dried in a vacuum oven at 20° C. for 12 hrs. SEM coupled with EDAX showed uniform silver coating on the membrane surface and within the pores. (Ag:S= 0.05:1)

Example 6

Electroless Coating of Silver Onto a Polyethersulfone membrane: (Method 5)

This example illustrates a method for depositing metallic silver onto a surface and within the pores of a membrane filter. A polyethersulfone membrane (Gelman Supor 450, pore size 0.45 mM, hydrophilic) was precut into a 47 mm disk. This membrane was immersed in 5 ml of a solution containing 1 g tin (II) chloride dihydrate (Aldrich), 1 ml concentrated HCl and 9 ml distilled water, at room temperature for 5 mins. The membrane was dried and immersed in the silver coating solution, described in Example 7B, which was then heated to 55° C. and maintained at this temperature for 3 mins. Rapid deposition of metallic silver on the membrane surface ensued. The plated membrane was thoroughly rinsed with distilled water and dried in a vacuum oven at 20° C. SEM coupled with EDAX showed uniform silver coating on the membrane surface and within the pores. (Ag:S=0.3:1)

Salts of other metals including titanium, vanadium, chromium, manganese, iron, cobalt, nickel, copper, zinc, germanium, selenium, zirconium, niobium, molybdenum, technetium, ruthenium, rhodium, palladium, antimony, tellurium and lead may be used as activators in place of tin dichloride prior to silver plating.

Example 7

Preparation of Silver Coating Solutions (A) This example illustrates the preparation of the silver coating solution that is used in Examples 2, 3, 4 and 10. 3 ml of a silver nitrate solution (10 g silver nitrate dissolved in 10 ml distilled water) was added to 3 ml of a sodium hydroxide solution (10 g sodium hydroxide dissolved in 10 ml distilled water) at 22° C. A brown precipitate of silver oxide formed rapidly. Concentrated ammonium hydroxide (28% ammonia, obtained from EM Science of Gibbstown, N.J.) was added dropwise to the solution until the silver oxide dissolved completely to give a clear solution of a soluble silver amine complex with a pH of 12.

(B) This example illustrates the preparation of the silver coating solution that is used in Examples 5 and 6. Three (3) ml of a sodium tartrate solution (tartaric acid disodium salt dehydrate, obtained from Aldrich) dissolved in 20 ml distilled water) was added to 3 ml of a silver nitrate solution (silver nitrate dissolved in 10 ml distilled water) at 22° C. A white precipitate of silver tartrate formed rapidly. Concentrated ammonium hydroxide, 28% ammonia (obtained from EM Science), was added dropwise to the solution until the silver tartrate dissolved completely to give a clear solution of ammoniacal silver tartarate with a pH of approximately 12.

Example 8

Oxygen Plasma Treatment of Silver Coated Membrane Filters

This example illustrates a method for treating a silver coated membrane filter with oxygen plasma so as to produce a silver oxide coating. A silver coated polyethersulfone membrane, obtained from either Example 1 or 2, was mounted on a glass holder and placed inside the reaction chamber of a plasma reactor so that both surfaces of the filter were exposed to the plasma. The reaction chamber was purged with oxygen three times. The pressure of the chamber was adjusted to 300 mTorr, the power maintained at 100 watts, and the membrane subjected to oxygen plasma for 2 mins.

Example 9

Surface Modification of Silver Coated Membrane Filters

This example illustrates a method for treating a silver coated membrane filter with a second compound that has anti-bacterial or anti-viral properties, 3.44 mg (20 mmol) of benzalkoniumchloride thiol (BAC-S), obtained as described in Example 9, was dissolved in 5 ml of absolute ethanol that was degassed for 1 hr under dry nitrogen. A freshly silver coated polyethersulfone membrane obtained from Example 1 or 2, was immersed in this solution at 22° C. for 16 hrs, rinsed in absolute ethanol, and dried under a stream of nitrogen.

Example 10

Synthesis of Benzalkoniumchloride Thiol (BAC-S)

This example illustrates a method for the synthesis of BAC-S from 10-chlorodecanethiol which in turn is synthesized from w-chlorodecane-thioacetate.

(a) ω-Chlorodecanethioacetate

Triphenylphosphine (6.53 g, 25 mmol) (obtained from Aldrich) was dissolved in 95 ml of dry, distilled tetrahydrofuran and the solution was cooled to 0° C. under dry nitrogen. 4.9 ml (25 mmol) of di-isopropylazodicarbonate (obtained from Aldrich) was added to the solution. The reaction mixture was stirred for 30 min. at 0° C. during which time a white precipitate formed. A 1M solution of 10-chloro-1-decanol (4.82 g in 25 ml THF (tetrahydrofuran) (obtained from VWR Scientific of Boston, Mass.) was added. 2.3 g of thiolacetic acid (obtained from Aldrich) in 20 ml THF was subsequently added. The resulting clear solution was stirred at 0° C. for 15 mins and warmed to room temperature. Two drops of water were added. The solvent was removed under reduced pressure, the residue was dissolved with ethyl ether and crystals of triphenylphosphine oxide were removed by filtration. Evaporation of the ether resulted in the crude product, ω-chlorodecanethioacetate, as a yellow oil. This product was distilled under reduced pressure (92°–95° C./10 mM) to give the pure compound as a pale yellow oil (3.23 g, 57%). IR neat, KBr plates cM-1: 1728,s, (O=C—S), TLC, silica (hexane:dichloromethane, 60:40 eluent) Rf=0.7.

(b) 10-Chlorodecanethiol

ω-Chlorodecanethioacetate (3.2 g, 1.2 mmol) was hydrolyzed in 30 ml of methanol, that was degassed under dry nitrogen for 4 hrs, containing 1.6 g (1.2 mmol) anhydrous potassium carbonate (obtained from Aldrich) at 22° C. The suspension was stirred for 1 hr, and then quenched with 0.75 ml glacial acetic acid (obtained from VWR Scientific). The potassium carbonate was filtered and the solvent removed under reduced pressure to yield 10-chlorodecanethiol as a pale yellow oil, 2.4 g, 1.1 mmol). TLC, silica (hexane:dichloromethane, 60:40 eluent) Rf=O (c) Benzalkoniumchloride Thiol (BAC-S)

2.4 g (11 mmol) of 10-chlorodecanethiol was reacted with 1.8 g (14 mmol) of N,N-dimethylbenzylamine (obtained from Aldrich) in 50 ml of dry THF. The reaction mixture was refluxed for 20 hrs and cooled. White crystals of BAC-S separated out. These crystals were filtered, washed with THF and dried, yielding 0.85 g of product.

Example 11

Synthesis of Alkane Thiol Derivative of Polyhexamethylene Biguanide (PHMB-S) and Chain Extended Polyhexamethylene Biguanide (PHMBCE-S)

This example illustrates a method of the synthesis of alkane thiol derivative of polyhexamethylene biguanide (PHMB-S) and chain extended polyhexamethylene biguanide (PHMBCE-S):

(a) Neutralization of Polyhexamethylene biguanide-bis hydrochloride

Polyhexamethylene biguanide-bis-hydrochloride (Zeneca, Wilmington, Del.), 1 g, was neutralized by addition of 2 ml. of a 10% NaOH solution. The solvent was evaporated and the residual solid was washed rapidly with water to minimize dissolution and dried to give polyhexamethylene biguanide (PHMB).

(b) Synthesis of Chain extension of chain polyhexamethylene biguanide (PHMBCE)

Polyhexamethylene biguanide (PHMB) was reacted with ethyleneglycol-bis-glycidylether (Aldrich) in a 1:0.9 mole ratio respectively in anhydrous DMSO at 50 deg.C. for 12 hours. The solvent was evaporated under reduced pressure and the solid residue was washed with ether and dried.

(c) Synthesis of alkanethiol derivative of polyhexamethylene biguanide (PHMB-S) and chain extended polyhexamethylene biguanide (PHMBCE-S)

Polyhexamethylene biguanide (PHMB-S) and chain extended polyhexamethylene biguanide (PHMBCE-S) respectively 1 mole equivalent) were reacted with 10-chlorodecanethiol (0.5 mole equivalent) described in Example 10b in anhydrous DMSO at 50 deg.C for 12 hours. The solvent was evaporated under reduced pressure and the solid residue was washed with ether and dried to yield the title compounds.

Example 12

Electroless Coating of Silver Onto Tubing For Use in Nozzle Assembly

This example illustrates a method for depositing silver onto the inner surface of tubing which can be used for the passageway walls in the nozzle assembly of the liquid dispenser. Polyethylene tubing (2 inches long, 800 mM ID) (obtained from Putnam Plastics Corp. of Dayville, Conn.) was immersed in a 25% aq. glutaraldehyde solution and ultrasonicated at 20° C. for 2 mins. The tubing was then dried thoroughly and silver coating solution, as described in Example 7A, was drawn into the tubing with a pipette. The plating solution was allowed to soak inside the tubing for 3 mins at 20° C., the excess solution was then expelled and the inside of the tubing was flushed with distilled water. A uniform silver coating resulted on the inside surface of the tubing.

The tubing was tested for bacteriocidal activity. Control or silver treated plastic tubing was inoculated with 10 mls of a suspension of *Pseudomonas dimunata* containing $5 \times 10^7$ organisms. The tubes containing bacterial suspension were incubated 15 hours at 37° C., at which time the tubes were placed in thioglycollate bacterial culture medium (1 cc) and vortexed. Aliquots of this solution were removed and serially diluted and 100 mls of these dilutions were plated onto NZY agar plates. The plates were incubated overnight at 37° C. and the bacterial concentrations were determined by counting bacterial colonies.

Example 13

Surface Modification of Silver Plated Membrane to Give Hydrophobic/Hydrophilic Surface Method A This example illustrates a method for producing a silver coated membrane filter that is partially hydrophobic and partially hydrophilic. 20.2 mg (20 mmol) of 1-dodecanethiol (obtained from Sigma Chemical Co., St. Louis, Mo.) was dissolved in 5 ml of absolute ethanol that was degassed for 1 hr under dry nitrogen. A freshly silver coated (by MVD or electroless process) polyethersulfone membrane (Gelman Supor 400, pore size 0.45 mM, hydrophilic) was partially immersed in this solution at 22° C. for 16 hours. The membrane was then rinsed in absolute ethanol and dried under a stream of nitrogen. The resulting surface treated membrane was hydrophobic (non-wetting) in the area treated with the alkyl thiol while remaining hydrophilic in the non-treated area.

Method B

This example illustrates a method for producing a partially hydrophobic area in a hydrophilic membrane (with or without a silver coating).

The hydrophilic membrane was immersed in a 2% n-hexane solution containing a 1:1:1 mixture (by weight) of methyltriacetoxy silane, ethyltriacetoxysilane and silanol terminated polytrimethylsiloxane (obtained from Huls America, Piscataway, N.J.). The membrane was air dried at room temperature for 30 min., after which it was heated at 120° C. for 30 min. to render the treated area totally hydrophobic.

Example 14

Silver Coating of Polymethylmethacrylate (PMMA) Sheets

This example illustrates methods for depositing metallic silver onto the surface of PMMA sheets.

Method A

A commercially obtained PMMA sheet was cut in the form of a slide and the surface was cleaned by ultrasonication in absolute ethanol for 1 minute at room temperature. The cleaned slide was then immersed in 30 ml of an activator solution consisting of 10% tin dichloride dihydrate ($SnCl_2 2H_2O$, obtained from Allied Chemicals of New York, N.Y.), 45% absolute ethanol and 45% distilled water and ultrasonicated at 45° C. for 15 minutes. The slide was rinsed several times with distilled water. It was then immersed in a 10% aqueous solution of silver nitrate for 15 minutes at room temperature. During this time the slide acquired a brown tinge due to the deposition of silver. The coated slide was then rinsed with distilled water and dried. The silver coating was adherent to the polymer and did not cause loss of transparency of the slide.

Method B

A PMMA slide was treated with plasma as described in Example 8, followed by immersion into a 2% aqueous solution of polyethyleneimine (PEI) (Aldrich Chemical Co., Milwaukee, Wis.) for 15 min. The slide was rinsed with water, after which it was first immersed in a 5% aqueous glutaraldehyde solution (Aldrich) for 5 min., followed by a 10% silver nitrate solution for 5 min. The surface was then subjected to electroless silver plating in a silver tartarate solution as described in Example 7B to give a uniform, adhesive silver mirror.

Example 15

Silver Coating of Polypropylene (PP)

This example illustrates a method for depositing a metallic silver coating onto the surface of polypropylene slides (obtained from Eastman Chemical Product, Inc. Kingsport, Tenn.). The slides were immersed in 30 ml of a 5% solution of chlorosulfonic acid (obtained from Aldrich of Milwaukee, Wis.) in chloroform at 50° C. for 5 mins. They were allowed to dry for 15 mins. then immersed in a 1M aqueous solution of sodium hydroxide after which they were rinsed thoroughly with distilled water. The surface treated slides were subjected to the silver coating procedure described in Example 4 using the plating solution described in Example 7B. This resulted in a uniform silver coating that is adherent to the polypropylene surface.

Example 16

Modification of Metallic Surfaces with Antimicrobial Compounds Generation of Adherent Silver Halide Surfaces Method A Freshly silver plated membranes (by MVD or electroless method) were exposed to either vapors of chlorine gas (generated in situ by reaction of sodium hypochlorite with concentrated HCl) or to bromine vapors for 0.5 to 1 min. at room temperature. The metallic surface was rapidly coated with a layer of silver chloride and silver bromide respectively. The membranes were then washed with water and dried.

Method B

Freshly silver plated membranes (by MVD or electroless method) were immersed in (i) an aqueous solution of 0.9% NaCl, or (ii) a 2% aqueous solution of bromine, or (iii) a 2% aqueous solution consisting of equimolar amounts of bromine, iodine and potassium iodide at room temperature for 15 minutes. A rapid coating of silver halide (or halides) resulted on the surface of the metallic coating. The membranes were then washed with water and dried.

Method C

Freshly silver plated membranes (by MVD or electroless method) were immersed in a 2% aqueous solution consisting of equimolar amounts of iodine and potassium iodide at room temperature for 15 minutes. A rapid coating of silver iodide resulted on the surface of the metallic coating. The membranes were then washed with ethanol followed by water and dried.

Modification of silver plated membrane with antimicrobial (a) with benzalkoniumchloridethiol (BAC-S): 3.44 mg ($10^{-3}$ mmol) of benzalkoniumchloridethiol (BAC-S) was dissolved in 5 ml of absolute ethanol that was degassed for 1 hr under dry nitrogen. A freshly silver coated (by MVD or electroless process) polyethersulfone membrane (Gelman Supor 450, pore size 0.45 mM, hydrophilic) was immersed in the resulting solution at 22 deg. C. for 16 hours. The membrane was then rinsed in absolute ethanol and dried under a stream of nitrogen.

(b) with alkanethiol derivative of polyhexamethylene biguanide (PHMBCE-S): 3 mg of polyhexamethylenebiguanide (PHMB-S) and chain extended polyhexamethylenebiguanide (PHMBCE-S) respectively were dissolved in 5 ml of degassed water. A freshly silver coated (by MVD or electroless process) polyethersulfone membrane (Gelman Supor 450, pore size 0.45 uM, hydrophilic) was immersed in the resulting solution at 22 deg. C. for 16 hours. The membrane was then rinsed with water, 1% HCl solution followed by water and dried.

Modification of gold foil with antimicrobial

Commercially obtained gold foil was treated with oxygen plasma for 3 minutes to clean the surface and improve wetability. The foil was then immersed in the resulting solution at 22 deg. for 16 hours. The membrane was then rinsed in absolute ethanol and dried under a stream nitrogen.

Modification of silver and gold surfaces with biguanides

Freshly silver plated membranes and gold foil (cleaned as described above) were immersed in aqueous solutions of diamine terminated polyhexamethylenebiguanide (ICI Zeneca) its chain extended analog (synthesized) that were suitably modified to incorporate a thiol group at 22 deg. C. for 16 hours. The membrane was then rinsed with water followed by a 1% HCl solution. After rinsing thoroughly with water they were dried.

Example 17

Modification of Silver halide surfaces with biguanides

Membranes coated with silver halides were immersed in either one of the coating solutions (Examples 18a or 18b) for 1 minute, excess solution removed from the membrane surface, after which they were allowed to dry at ambient temperature for 0.5 hour. The membrane was then cured at 130° C. for 30 minutes. It was then extracted with a 50% aqueous ethanol solution for 30 minutes at 80° C., followed by 3 times with water (1 hour each, 80° C.) after which they were air dried for 0.5 hour at 80° C. The coated membranes were then immersed in a solution containing 0.5% of silver iodide and 12.5% (wt/vol.) potassium iodide in 100 mL of 50% aqueous ethanol at ambient temperature for 5 minutes. The membranes were rinsed with 50% aqueous ethanol followed by water extraction (3×100 mL, 1 hour each at 80° C. They were then air dried.

Example 18

Preparation of biguanide coating solutions

Polyhexamethylenebiguanide (PHMB) was precipitated from a 20% aqueous solution of polyhexamethylene biguanidedihydrochloride ((Zeneca Biocides, Wilmington, Del.) by addition of two volume equivalents of 5% aqueous NaOH. The resulting precipitate was separated from the alkaline solution, dissolved in anhydrous DMF and reprecipitated with acetonitrile. The precipitate was filtered and dried under vacuum at 50° C. for 6 hours.

(a) 2 mL of a 5% (weight/volume) PHMB solution in anhydrous ethanol was added to 2 mL of 5% (weight/volume) solution of 4,4'-methylene-bis(N,N-diglycidylaniline) (Aldrich Chemical Company, Milwaukee, Wis.) dissolved in a 4:1 (vol/vol) ethanol/acetonitrile mixture. The solution was stirred at room temperature for 20 minutes and diluted with 76 mL of anhydrous ethanol to a solution containing 0.25% solids.

(b) 2 mL of a 5% (weight/volume) PHMB solution in anhydrous ethanol was added to 2 mL of 5% (weight/volume) solution of 4,4'-methylene-bis(N,N-diglycidylaniline) (Aldrich Chemical Company, Milwaukee, Wis.) dissolved in a 4:1 (vol/vol) ethanol/acetonitrile mixture. The solution was refluxed at 90°–95° C. for 15 minutes. The solution was cooled and diluted with 76 mL of anhydrous ethanol to a solution containing 0.25% solids.

(c) 2 mL of a 5% (weight/volume) PHMB solution in anhydrous ethanol was added to 2 mL of 5% (weight/volume) solution of 4,4'-methylene-bis(N,N-diglycidylaniline) (Aldrich Chemical Company, Milwaukee, Wis.) dissolved in a 4:1 (vol/vol) ethanol/acetonitrile mixture. The solution was refluxed at 90°–95° C. for 15 minutes. The solution was cooled diluted with 16 mL of anhydrous DMF. 50 mg of finely ground silver iodide was dispersed in the diluted solution and the resulting suspension was heated to 80° C. with stirring to produce a clear solution. This was cooled and filtered to give a clear, homogeneous solution (d) 2 mL of a 5% (weight/volume) PHMB solution in anhydrous ethanol was added to 2 mL of 5% (weight/volume) solution of 4,4'-methylene-bis(N,N-diglycidylaniline) (Aldrich Chemical Company, Milwaukee, Wis.) dissolved in a 4:1 (vol/vol) ethanol/acetonitrile mixture. The solution was refluxed at 90°–95° C. for 15 minutes. The solution was cooled diluted with 16 mL of anhydrous DMF. 50 mg of finely ground silver iodide was dispersed in the diluted solution to give a well dispersed suspension.

Example 19

Introduction of Antimicrobial Compounds on Silylated Surfaces

The following reaction schemes demonstrate methods for preparing a silylated surface and reacting an antimicrobial agent to the silyl functionality.

I) Direct coupling reactions

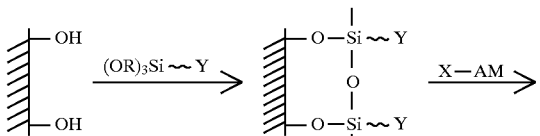

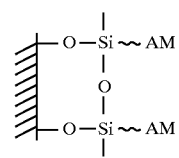

X, Y = reactive functionalities (e.g., Y = △, —NH$_2$, —OSO$_2$CF$_3$,

X = —NH$_2$, △); AM = antimicrobial (e.g., BAC, PHMB)

II) Grafting from reactions

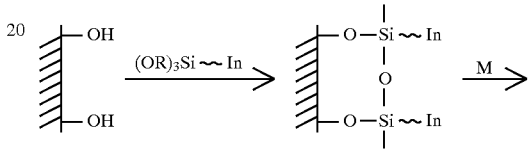

In = Initiating group
M = Reactive monomer
AM = antimicrobial compound

For example, In = ⬡—N, R$_3$P, M = ⬡—N$_+$—R X$^-$,

AM = BAC, PHMB wherein X = —OSO$_3$CF$_3$, and R = H or an alkyl group.

III) Grafting to reactions

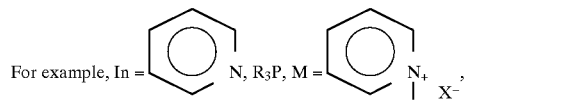

AM = antimicrobial

IV) Dendrimer type reactions

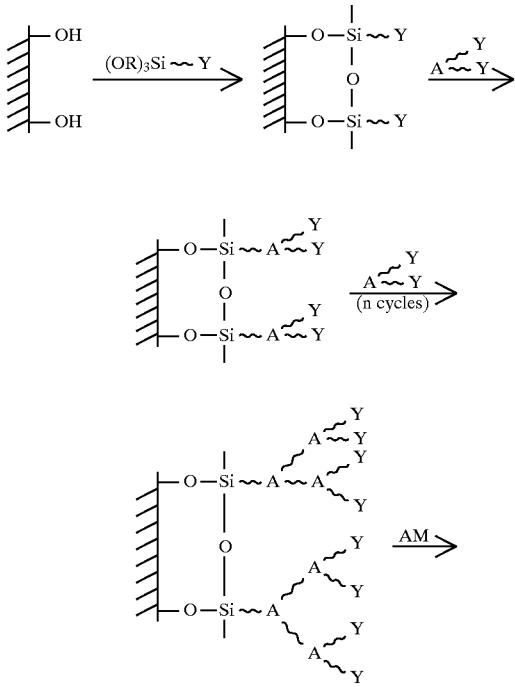

Y = OSO$_2$CF$_3$, A = HN—, AM = antimicrobial

Example 20

Introduction of Antimicrobial Compounds on Non-Silylated Surfaces Incorporation of silver salts on PMMA surfaces I) Polyacrylic acid was introduced on the surface of PMMA by graft polymerization of acrylic acid to obtain surface functionalization. Base treatment followed by an aqueous silver nitrate solution resulted in the formation of silver salt of polyacrylic acid II) The polyacrylic acid coating obtained on PMMA by the above method was further modified by coupling the carboxylic groups of the acrylic acid with cysteine using DCC. The membrane was then treated with base followed by an aqueous silver nitrate solution to give a mixture of silver carboxylate and silver thiolate.

Attachment of antimicrobials to coulombic multilayers on activated-polymeric surfaces Polymeric surfaces activated by (i) oxidative chemical procedures, (ii) plasma or (iii) e-beam are then treated sequentially with polyethyleneimine (PEI) and polyacrylic acid. This process may be repeated over several cycles to obtain the desired amplification. Antimicrobial compounds (or suitably modified derivatives thereof) are then covalently attached to the amine functionalities in PEI.

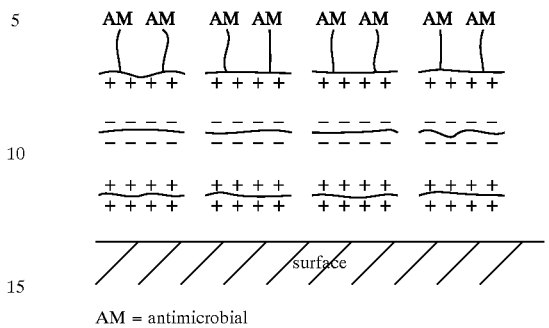

AM = antimicrobial

Coating of antimicrobials to activated polymeric surfaces

Polymeric surfaces are activated by (i) oxidative chemical methods or (ii) plasma. Solutions of antimicrobial compounds (or suitably modified derivatives thereof) are then applied on the surfaces and cured (thermally, photochemically or chemically) to result in stable, non leachable coatings

Example 21

Antimicrobial Coating of Polymeric Surface (a) Polypropylene coupons (10×10 cm) were surface oxidized by known methods (chemical or plasma). The coupons were immersed in the coating solution described in Example 18a or 18b for 1 minute, excess solution removed from the membrane surface, after which it was allowed to dry at ambient temperature for 0.5 hour. The coupons were then cured at 130° C. for 30 minutes. They were then extracted with a 50% aqueous ethanol solution for 30 minutes at 80° C., followed by 3 times with water (1 hour each, 80° C.) after which they were air dried for 0.5 hr. at 80° C. The coated membranes were then immersed in a solution containing 0.5% of silver iodide and 12.5% (wt/vol.) potassium iodide in 100 mL of 50% aqueous ethanol at ambient temperature for 5 minutes. The membranes were rinsed with 50% aqueous ethanol followed by water extraction (3×100 mL, 1 hour each at 80° C. They were then air dried.

(b) Polypropylene coupons (10×10 cm) were surface oxidized by known methods (chemical or plasma). The coupons were immersed in the coating solution described in Examples 18c or 18d for 1 minute, excess solution removed from the surface, after which it was allowed to dry at ambient temperature for 0.5 hour. The coupons were then cured at 130° C. for 30 minutes. They were then extracted with a 50% aqueous ethanol solution for 30 minutes at 80° C., followed by 3 times with water (1 hour each, 80° C.) after which they were air dried for 0.5 hr. at 80° C.

Example 22

Preparation of surface coating solutions (a) 2 mL of a 5% (weight/volume) PHMB solution in anhydrous ethanol was added to 2 mL of 5% (weight/volume) solution of 4,4'-methylene-bis(N,N-diglycidylaniline) (Aldrich Chemical Company, Milwaukee, Wis.) dissolved in a 4:1 (vol/vol) ethanol/acetonitrile mixture. The solution was refluxed at 90°–95° C. for 15 minutes.

The solution was cooled diluted with 16 mL of anhydrous DMF. 50 mg of finely ground silver iodide was dispersed in the diluted solution and the resulting suspension was heated to 80° C. with stirring to produce a clear solution. This was cooled and filtered to give a clear, homogeneous solution.

(b) 2 mL of a 5% (weight/volume) PHMB solution in anhydrous ethanol was added to 2 mL of 5% (weight/volume) solution of 4,4'-methylene-bis(N,N-diglycidylaniline) (Aldrich Chemical Company, Milwaukee, Wis.) dissolved in a 4:1 (vol/vol) ethanol/acetonitrile mixture. The solution was refluxed at 90°–95° C. for 15 minutes. The solution was cooled diluted with 16 mL of anhydrous DMF. 50 mg of finely ground silver iodide was dispersed in the diluted solution to give a well dispersed suspension.

Example 23

Anti-bacterial Properties of Differently Treated Membrane Filters

This example illustrates a method for testing different types of membrane filters with different pore sizes, which have been coated with different compounds by different procedures, for their bacteriocidal/bacteriostatic properties.

Filters, either control or treated, were placed into Gelman plastic filter holders and the entire unit was autoclaved 30 minutes at 121RC. Using aseptic techniques under a laminar flow hood, sterile bacterial media, sterile saline solution or a preservative free artificial tear solution ("Tears Plus," obtained from Johnson and Johnson) was introduced to eliminate air pockets and to ensure proper flow through the assembled filter apparatus. The challenge organism, either *Pseudomonas dimunata, Candida albicans* or a "cocktail" consisting of (i) *Pseudomonas dimunata, Bacillus subtilis,* and *Escherichia coli*, or (ii) *Staphylococcus aureus* and *Pseudomonas aeruginosa* at a concentration of $10^7$ organisms per ml, was purged through the filter using a 3 cc syringe and manual pressure. Approximately 1 mL of liquid was expelled first and was checked for sterility so to ensure that the membrane was properly sealed. Three drops of eluate were collected and tested for sterility. The outlet tip was maintained in a sterile environment using a clean sterile cover and the entire unit was stored at 37° C. for the course of the experiment. The sterility of the eluate was tested daily by collecting three drops (approximately 150 ml) of bacteria/media inoculum into sterile thioglycollate medium which was then placed in a 37° C. shaker overnight and assessed the next day for sterility. As the medium/bacteria inoculum level lowered over the course of the experiment, the input syringe was removed and fresh sterile media was added and reattached to the filter holder unit. A filter was considered to have "failed" when the sterility check failed on two consecutive tests, the failed filter apparatus still held air pressure under water, and the failed sterility check demonstrated by gram stain the expected morphology of the test organism.

Table I summarizes the results. "GS" is Gelman Supor 400 membranes; "GH" is Gelman HT650 membranes; "M" is Millipore membranes. The type of material that the membranes are composed of is indicated by "PES" for polyethersulfone and "PVDF" for polyvinylidene fluoride. "mM" indicates the micron pore size of the membrane. "-" indicates that the membrane was untreated. "MVDAG" indicates the membrane was treated to produce a silver coating by the metal vapor deposition method as described in Example 1. "TAg" indicates the membrane was treated to produce a silver coating by the electroless method of this invention as described in Example 2, Method 1. "+P" indicates the silver coated membrane was treated with oxygen plasma to produce a silver oxide coating as described Example 7. "+B" indicates that the silver coated membrane was treated with BAC-S (benzalkoniumchloride thiol) to produce a layer of BAC-S over the silver coating as described in Example 8. "+BG" indicates that the silver coated membrane was treated with PHMB-S or PHMBCE-S. "+Cl" indicates that the membrane was treated with chlorine or NaCl. "+Br" indicates that the membrane was treated with bromine. "+Br+I" indicates that the membrane was treated with a mixture of bromine and iodine. "+I" indicates that the membrane was treated with iodine. "+I+PHMB" indicates that the silver iodide coated membrane additionally with a PHMB coating. "+PHMB" indicates that the membrane was coated with PHMB. "+PHMB+I" indicates that the membrane was coated with PHMB followed by silver iodide introduction.

The numbers in the "Days" column indicate the average number of days until the filter failed, as determined by the criteria discussed above. A ">#" indicates that no failure was detected for the duration of the test, i.e., the number of days indicated.

The various growth media used are indicated by "B" for sterile bacterial media, "S" for sterile saline solution, and "T" for "Hypo Tears." a preservative free artificial tear solution by Johnson & Johnson. Sterilization of the membranes was achieved either by autoclaving at 121RC for 30 minutes ("A"), or placement in absolute ethanol for 20 minutes ("Et"). The "No." indicates the number of samples of membranes that were tested

TABLE 1

Bacterial Challenge Experiments on Silver Coated Membranes

| Mfgr | Type | mm | Treatment | Days | Growth Medium | Sterilzation | No. |
|---|---|---|---|---|---|---|---|
| GS | PES | 0.45 | — | 7 | B | A | 3 |
| GS | PES | 0.45 | MVDAG + P | 10 | B | A | 3 |
| GS | PES | 0.45 | TAg | 22 | B | A | 3 |
| GS | PES | 0.45 | TAG + P | 16 | B | A | 3 |
| GS | PES | 0.45 | MVDAG + B | 14 | B | A | 3 |
| GS | PES | 0.45 | TAG + B | >77 | B | A | 3 |
| GS | PES | 0.45 | | 7 | B | A | 9 |
| GS | PES | 0.45 | TAg | >25 | B | A | 6 |
| GS | PES | 0.45 | | 10 | T | A | 9 |
| GS | PES | 0.45 | TAg | >175 | T | A | 9 |
| GS | PES | 0.45 | | 3 | S | A | 6 |
| GS | PES | 0.45 | TAg | >57 | S | A | 6 |
| GH | PES | 0.65 | | 4 | T | A | 3 |
| GH | PES | 0.65 | TAg | >82 | T | A | 3 |
| GS | PES | 0.65 | | 1 | S | A | 5 |
| GS | PES | 0.65 | TAg | >145 | S | A | 5 |
| m | PVDF | 0.22 | | 5 | B | Et | 1 |
| m | PVDF | 0.22 | MVDAG | >14 | B | Et | 1 |
| m | PVDF | 0.22 | MVDAG + P | >14 | B | Et | 1 |
| m | PVDF | 0.22 | TAg | >14 | B | Et | 1 |
| m | PVDF | 0.22 | TAg + p | >14 | B | Et | 1 |
| m | PVDF | 0.22 | TAG + B | >14 | B | Et | 1 |
| m | PVDF | 0.22 | | 15 | B | A | 3 |
| m | PVDF | 0.22 | TAg | >170 | B | A | 3 |
| GS | PBS | 0.45 | TAg + B | >71 | S | A | 3 |
| GS | PES | 0.45 | THE + I + PHMB | >97 | S | Et | 3 |
| GS | PES | 0.65 | TAG + B | >71 | S | A | 3 |
| GS | PES | 0.65 | TAG + BG | >71 | S | A | 3 |
| GS | PES | 0.65 | TAG + Cl | >62 | S | A | 3 |
| GS | PES | 0.65 | TAG + Br | >36 | S | A | 25 |
| GS | PES | 0.65 | TAG + Br + I | >20 | S | A | 15 |

TABLE 1-continued

Bacterial Challenge Experiments on Silver Coated Membranes

| Mfgr | Type | mm | Treatment | Days | Growth Medium | Sterilization | No. |
|---|---|---|---|---|---|---|---|
| m | PVDF | 0.45 |  | 2 | B | Et | 1 |
| m | PVDF | 0.45 | MVDAG | 5 | B | Et | 1 |
| m | PVDF | 0.45 | MVDAG + P | >11 | B | Et | 1 |
| m | PVDF | 0.45 | TAg | >11 | B | Et | 1 |
| m | PVDF | 0.45 |  | 7 | B | A | 3 |
| m | PVDF | 0.45 | TAg | >70 | B | A | 3 |

Example 24

Anti-Microbial Properties of Differently Treated Substances

This example illustrates the anti-microbial effect of various substrates having immobilized thereon anti-microbial agents. The substrates include glass beads, polyethersulfone (PES) pellets, gold foil and PES membranes. The test was carried out as described in Example 20. The results are shown in Table 2.

TABLE 2

| | TYPE | MEDIUM | ORGANISM | COATING | COUNT 1(24 hrs) | NUMBER |
|---|---|---|---|---|---|---|
| 1 | Tear Soln (P)* | | PD | | 0 | |
| 2 | Tear Soln (PF)* | | PD | | $6.2 \times 10^3$ | |
| 3 | Glass Beads | A | PD | Uncoated | $1.0 \times 10^4$ | 7 |
| 4 | Glass Beads | A | PD | Silver coated | 63 | 7 |
| 5 | Glass Beads | A | PD | Uncoated | $2.3 \times 10^3$ | 2 |
| 6 | Glass Beads | A | PD | Silver coated | 33 | 2 |
| 7 | PES Pellets | A | PD | Uncoated | $4.0 \times 10^3$ | 25 |
| 8 | PES Pellets | A | PD | Silver coated | 0 | 25 |
| 9 | PES Pellets | A | PD | Uncoated | $2.0 \times 10^3$ | 5 |
| 10 | PES Pellets | A | PD | Silver coated | 2 | 5 |
| 11 | Tear Soln (P)* | A | BC1 | | 0 | |
| 12 | Tear Soln (PF)* | A | BC1 | | $3.5 \times 10^6$ | |
| 13 | PES Pellets | A | BC1 | Uncoated | $3.5 \times 10^6$ | 25 |
| 14 | PES Pellets | A | BC1 | Silver coated | 0 | 25 |
| 15 | PES Pellets | A | BC1 | Silver + Add. Coat.[1] | 0 | 25 |
| 16 | PES Pellets | B | BC1 | Uncoated | $8.0 \times 10^6$ | 25 (New beads) |
| 17 | PES Pellets | B | BC1 | Silver coated | 0 | 25 (New beads) |
| 18 | PES Pellets | B | BC1 | Uncoated | $8.0 \times 10^6$ | 25 (Used beads**) |
| 19 | PES Pellets | B | BC1 | Silver + Add. Coat.[1] | 0 | 25 (Used beads**) |
| 20 | PES Pellets | B | BC1 | Silver + Add. Coat.[2] | 0 | 25 (Used beads**) |
| 21 | Tear Soln (P)* | A | CA | | 0 | |
| 22 | Tear Soln (PF)* | A | CA | | $2.5 \times 10^4$ | |
| 23 | PBS Control | B | CA | | $8.4 \times 10^4$ | |
| 24 | PES Pellets | B | CA | Uncoated | $1.5 \times 10^5$ | 25 |
| 25 | PES Pellets | B | CA | Silver + Add. Coat.[2] | 10 | 25 |
| 26 | PES Pellets | B | CA | Silver + Add. Coat.[3] | $3.5 \times 10^2$ | 25 |
| 27 | Gold Foil | B | BC1 | Uncoated | $9.6 \times 10^5$ | 2.5 × 1.25+ |
| 28 | Gold Foil | B | BC1 | Silver + Add. Coat.[3] | 0 | 2.5 × 1.25+ |
| 29 | Gold Foil | B | BC1 | Silver + Add. Coat.[3] | 0 | 2.5 × 1.25+ |
| 30 | Gold Foil | B | CA | Uncoated | $7.4 \times 10^3$ | 2.5 × 1.25+ |
| 31 | Gold Foil | B | CA | Silver + Add. Coat.[2] | $1.6 \times 10^3$ | 2.5 × 1.25+ |
| 32 | Gold Foil | B | CA | Silver + Add. Coat.[3] | 0 | 2.5 × 1.25+ |
| 33 | Polypropylene (PP) | B | BC1 | | $1 \times 10^6$ | 2.5 × 1.25+ |
| 34 | Polypropylene (PP) | B | BC1 | Silver salt + Add. Coat.[4] | 0 | 2.5 × 1.25+ |
| 35 | Polypropylene (PP) | B | BC2 | Silver salt + Add. Coat.[4] | 0 | 2.5 × 1.25+ |
| 36 | Polypropylene (PP) | B | PSA | Silver salt + Add. Coat.[4] | 0 | 2.5 × 1.25+ |
| 37 | Polypropylene (PP) | B | BC1 | Silver salt + Add. Coat.[5] | 0 | 2.5 × 1.25+ |
| 38 | Polypropylene (PP) | B | BC2 | Silver salt + Add. Coat.[5] | 0 | 2.5 × 1.25+ |
| 39 | Polypropylene (PP) | B | BC1 | Silver salt + Add. Coat.[6] | 0 | 2.5 × 1.25+ |
| 40 | Polypropylene (PP) | B | BC2 | Silver salt + Add. Coat.[6] | 0 | 2.5 × 1.25+ |
| 41 | Polypropylene (PP) | B | PSA | Silver salt + Add. Coat.[6] | 0 | 2.5 × 1.25+ |
| Bacterial Challenge on 0.65 uM (Gelman PES, MT 650) membranes | | | | | | |
| 42 | PBS Control | | BC2 | | $2.5 \times 10^6$ | |
| 43 | 0.65 uM PES | B | BC2 | silver | 0 | 13 mm++ |
| 44 | 0.65 uM PES | B | BC2 | Silver salt | 0 | 13 mm++ |
| 1/30 Bacterial Challenge on 0.45 uM (Gelman PES, Super 450) membranes | | | | | | |
| 45 | 0.45 uM PES | B | BC1 | | $1 \times 10^6$ | 13 mm++ |
| 46 | 0.45 uM PES | B | BC2 | | $1 \times 10^6$ | 13 mm++ |
| 47 | 0.45 uM PES | B | BC1 | Silver salt + Add. Coat[4] | 0 | 13 mm++ |
| 48 | 0.45 uM PES | B | BC2 | Silver salt + Add. Coat[4] | 0 | 13 mm++ |
| 49 | 0.45 uM PES | B | PSA | Silver salt + Add. Coat[4] | 0 | 13 mm++ |
| 50 | 0.45 uM PES | B | BC1 | Silver salt + Add. Coat[5] | 0 | 13 mm++ |

TABLE 2-continued

| TYPE | MEDIUM | ORGANISM | COATING | COUNT 1(24 hrs) | NUMBER |
|---|---|---|---|---|---|
| 51 0.45 uM PES | B | BC2 | Silver salt + Add. Coat[5] | 0 | 13 mm[++] |
| 52 0.45 uM PES | B | PSA | Silver salt + Add. Coat[5] | 0 | 13 mm[++] |
| 53 0.45 uM PES | B | BC1 | Silver salt + Add. Coat[6] | 0 | 13 mm[++] |
| 54 0.45 uM PES | B | BC2 | Silver salt + Add. Coat[6] | 0 | 13 mm[++] |
| 55 0.45 uM PES | B | PSA | Silver salt + Add. Coat[6] | 0 | 13 mm[++] |

A: *Johnson & Johnson HypoTears Tear Solution
B: B: Phosphate Buffered Saline
(P) Preservative containing
(PF) Preservative free
Uncoated: No coating, control
Silver coated: Coated with metallic silver
Silver + Additional coating:
[1]Benzalkonium chloride thiol
[2]poly(hexamethylenebiguanide) thiol
[3]chain-extended poly(hexamethylene biguanide) thiol
[4]Silver halide + poly(hexamethylenebiguanide) overcoat
[5]Silver iodide + poly(hexamethylenebiguanide) coating solution
[6]Poly(hexamethylenebiguanide) coating followed by AgI/KI introduction
Silver salt: Inorganic salt of silver halide salts such as chloride or bromide or mixed salts of chloride, bromide and iodide
Avg. surface area of each bead: 0.07 cm$^2$
Avg. surface area of each pellet: 0.02 cm$^2$
BC1: Cocktail contains *p. dimunuta, B. subtlis,* and *E. Coli*
BC2: Cocktail contains *S. aureus* and *p. aeruginosa*
PD: *Pseudomonmas dimunate*
PSA: *Pseudomonas aeruginosa*
CA *Candida albicans*
**Stored for one month
[+]Dimension of foil (cm)
[++]Membrane diameter Equivalents Those skilled in the art will be able to ascertain, using no more than routine experimentation, many equivalents of the specific embodiments of the invention described herein. These and all other equivalents are intended to be encompassed by the following claims.

What is claimed is:

1. A liquid composition for applying a non-leachable antimicrobial layer or coating on a surface, comprising a solution, dispersion or suspension of a biguanide polymer, a cross-linker reacted with the biguanide polymer to form an adduct, and an antimicrobial metal, metal salt or metal complex, wherein said metal, metal salt or metal complex forms a complex with said adduct, and wherein said antimicrobial layer or coating does not release biocidal levels of leachables into a contacting solution.

2. The liquid composition of claim 1 wherein the biguanide polymer is polyhexamethylene biguanide or a polymer containing biguanide moieties.

3. The liquid composition of claim 1 wherein the metal is silver.

4. The liquid composition of claim 1 wherein the crosslinker is an organic compound containing reactive groups selected from the group consisting of isocyanates, carboxylic acids, acid chlorides, acid anhydrides, succimidyl ether, aldehydes, and ketones, or an organic compound selected from the group consisting of alkyl methanesulfonates, alkyl trifluoromethanesulfonates, alkyl paratoluenemethanesulfonates, alkyl halides and organic multifunctional epoxides.

5. The liquid composition of claim 1 wherein the metal salt is silver iodide.

6. A liquid composition for applying an antimicrobial layer or coating on a surface, comprising a solution, dispersion or suspension of polyhexamethylene biguanide, a cross-linker reacted with the biguanide polymer to form an adduct, and a silver salt, wherein said silver salt forms a complex with said adduct, and wherein said antimicrobial layer or coating does not release biocidal levels of leachables into a contacting solution.

7. The liquid composition of claim 6 wherein the silver salt is silver iodide.

8. The liquid composition of claim 6 further comprising wherein the polyhexamethylene biguanide is reacted with an epoxide to form an adduct.

9. The liquid composition of claim 8 wherein the epoxide is 4,4'-methylene-bis(N,N-diglycidylaniline).

* * * * *

UNITED STATES PATENT AND TRADEMARK OFFICE
CERTIFICATE OF CORRECTION

PATENT NO.    : 5,869,073
DATED         : February 9, 1999
INVENTOR(S)   : Sawan et al.

It is certified that error appears in the above-identified patent and that said Letters Patent is hereby corrected as shown below:

At column 1, line 14, above "FIELD OF THE INVENTION", insert:

-- STATEMENT OF GOVERNMENT RIGHTS

This invention was made with government support under Grant No. EY10787, awarded by the Department of Health and Human Services (National Institutes of Health - National Eye Institute). The government has certain rights in the invention. --

Signed and Sealed this

Fourteenth Day of March, 2000

*Attest:*

Q. TODD DICKINSON

*Attesting Officer*     Commissioner of Patents and Trademarks